(12) United States Patent
Rossel

(10) Patent No.: US 12,727,928 B2
(45) Date of Patent: Sep. 8, 2026

(54) CRYOGENIC DEVICE AND ACTUATOR ASSEMBLY THEREIN

(71) Applicant: Oystershell NV, Merelbeke (BE)

(72) Inventor: Bart Rossel, Merelbeke (BE)

(73) Assignee: Oystershell NV, Merelbeke (BE)

(*) Notice: Subject to any disclaimer, the term of this patent is extended or adjusted under 35 U.S.C. 154(b) by 733 days.

(21) Appl. No.: 17/415,293

(22) PCT Filed: Dec. 20, 2019

(86) PCT No.: PCT/EP2019/086772
§ 371 (c)(1),
(2) Date: Jun. 17, 2021

(87) PCT Pub. No.: WO2020/128027
PCT Pub. Date: Jun. 25, 2020

(65) Prior Publication Data

US 2022/0061903 A1 Mar. 3, 2022

(30) Foreign Application Priority Data

Dec. 20, 2018 (EP) .................................... 18214918
Jun. 21, 2019 (EP) .................................... 19181729

(51) Int. Cl.
*A61B 18/02* (2006.01)
*A61B 18/00* (2006.01)

(52) U.S. Cl.
CPC *A61B 18/0218* (2013.01); *A61B 2018/00297* (2013.01); *A61B 2018/0047* (2013.01); *A61B 2018/0262* (2013.01)

(58) Field of Classification Search
None
See application file for complete search history.

(56) References Cited

U.S. PATENT DOCUMENTS 5,275,595 A 1/1994 Dobak
6,226,996 B1 5/2001 Weber
(Continued)

FOREIGN PATENT DOCUMENTS

DE 19619257 A1 * 11/1997 ............. A61B 18/02
EP 0570301 A1 11/1993
(Continued)

OTHER PUBLICATIONS

ISR-WO dated Mar. 27, 2020 for parent application PCT/EP2019/086772.

*Primary Examiner* — Sean W Collins
*Assistant Examiner* — Nora W Rhodes
(74) *Attorney, Agent, or Firm* — Vorys, Sater, Seymour and Pease LLP

(57) ABSTRACT

The current invention concerns a device for the topical cryotherapy of dermatological disorders, the device comprising: a housing for holding a pressurized carbon dioxide cartridge; an applicator nozzle comprising (i) an internal channel for guiding the outflow of carbon dioxide from said pressurized carbon dioxide cartridge, and (ii) an applicator surface onto which carbon dioxide ice may be formed; and an actuator mechanism for controlling an outflow of carbon dioxide from said pressurized carbon dioxide cartridge to said applicator nozzle. The invention further concerns a cryogenic applicator pen comprising an actuator assembly for controlling an outflow of a cryogenic fluid, wherein said actuator assembly comprises at least one spring leaf, wherein said spring leaf on one side bears against a ball of a ball valve and on an opposite side bears against a positioning casing bearing a needle for piercing a cryogenic fluid cartridge. In a second aspect, the invention provides an actuator assembly suitable for cryogenic device for controlling an outflow of a cryogenic fluid, wherein said actuator assembly comprises at least one spring leaf and a needle, (Continued)

whereby said spring leaf is bearing against a ball of a ball valve, and whereby said actuator assembly is sealed to said cryogenic device by sealing o-rings.

9 Claims, 13 Drawing Sheets

(56) References Cited

U.S. PATENT DOCUMENTS

| | | | | |
|---|---|---|---|---|
| 10,779,885 | B2 * | 9/2020 | Kim | A61N 5/04 |
| 2004/0102768 | A1 | 5/2004 | Cluzeau | |
| 2004/0149338 | A1 | 8/2004 | Wheeler | |
| 2009/0018628 | A1 * | 1/2009 | Burns | A61N 1/403 607/101 |
| 2010/0168726 | A1 * | 7/2010 | Brookman | A61B 18/0218 606/22 |
| 2015/0313662 | A1 * | 11/2015 | Ottanelli | B65D 83/303 606/25 |

FOREIGN PATENT DOCUMENTS

| | | | | |
|---|---|---|---|---|
| FR | 2981639 | A1 | 4/2013 | |
| GB | 2253882 | A | 9/1992 | |
| WO | 2004042763 | A2 | 5/2004 | |
| WO | 2007/028975 | A1 | 3/2007 | |
| WO | 2014114696 | A1 | 7/2014 | |
| WO | WO-2016178161 | A1 * | 11/2016 | A61B 18/02 |
| WO | 2020/128027 | A1 | 6/2020 | |

* cited by examiner 101
104
110
100
105
106
106'
107
107'
111
112
300
301
302
303a
304
305
303b
306
200
401
402a
402b
400
201
202
404
406

205a
203
2012
306
305
2013
2011
202
201
204
205b

CRYOGENIC DEVICE AND ACTUATOR ASSEMBLY THEREIN

TECHNICAL FIELD

The present invention relates to cryogenic therapeutic devices and, in particular provides a device to facilitate in the application of cryogenic therapeutic treatments. In particular, the present invention provides an actuator assembly for cryogenic devices, for easier and cleaner application of a cryogenic fluid.

BACKGROUND

Cryosurgery is the destruction of tissues using the properties of freezing. The use of liquefied gas coolants to cool and freeze tissue has long been known. Commonly employed cryogenic fluids are liquid nitrogen and dimethyl ether/propane aerosol, nitrogen oxides, carbon dioxide and the like. The main agent used in medical treatment is liquid nitrogen. This is conveniently applied via the spraying of a cryogenic fluid or by applying a cotton bud saturated with the cryogenic fluid. Commonly employed cryogenic fluids are liquid nitrogen and dimethyl ether/propane aerosol (this formulation has previously been employed by a product known as Histofreezer™). This achieves a skin temperature of between zero and −50° C. It is well known to produce a cooling effect by the evaporation of a liquid. For example, dichlorotetrafluoroethane (also known as Frigiderm™ or Freon 114) has been used extensively in cosmetic surgery to cool and stiffen skin. An advantage of dichlorotetrafluoroethane is that under normal conditions its maximum skin cooling temperature is −40° C., even though its boiling point is +3.80° C. Ethyl chloride is an efficient skin refrigerant but has the undesirable qualities of being explosive when mixed with air, toxic to the liver, as well as being capable of causing general anesthesia upon inhalation by the patient or doctor.

It has been proven that colder cryorefrigerants (Cryosthesia −60° C. also known as dichlorodifluoromethane or Freon 12, boiling point −29.8° C.) can produce maximum skin cooling temperatures of −66° C., but care needs to be taken in the application, since improper use can cause unwanted tissue damage and resulting in serious complications, such a scarring, depigmentation and infection. Unfortunately, all of these chlorofluorocarbon refrigerants have been shown to damage the ozone layer and their use is now strictly controlled if not banned in many countries. Dry ice or frozen carbon dioxide has also been used to cool the skin. However, applying dry ice to an epidermal surface can quickly produce temperatures of close to −78° C.

"Dry ice" application has been shown to be destructive to the epithelium layer and is now more commonly used to improve the penetration of skin peeling chemicals by removing the epidermis just prior to peel-acid application. Because temperatures of −78° C. are rapidly approached with little room for manual control, direct solid state, "dry ice" contact is not a viable option for controlled cooling of skin prior to or during dermabrasion if the surgeon is to minimize thermal damage.

Certain cryosurgery procedures are applied prior to mechanical dermabrasion. The hardness of the skin freeze has been shown to be critical in controlling the depth of dermabrasion and classified as either superficial (0.2-0.5 mm), moderate (0.5-1.0 mm), or deep (1.5-2.0 mm) according to Ayres {Ayres S III: Superficial chemosurgery, including combined technique, using dermabrasion, in Epstein E, Epstein E Jr, editors: Skin surgery. Springfield, 111, 1982, Charles C Thomas, Publisher.} The skin temperatures achieved and thus the hardness of the skin is dependent upon the type of freezing agent, skin temperature prior to treatment, operating room temperature and numerous other factors. A recent and particularly valuable therapeutic use of cryogenics is to provide localized freezing of a part of a human or animal body in order to remove a wart or other growth from epidermal tissue. In this use, a refrigerant is maintained under pressure in a can and is dispensed, via a valve and an outlet tube, through a cotton wool bud or a polyurethane foam which collects the discharged cryogenic fluid which is placed on or near the site to be treated. Handheld, liquid nitrogen cryosurgical devices and other refrigerant devices have been used to treat a wide range of common skin lesions. Conditions commonly treated in general practice are: Verruca (warts), Actinic Keratoses, Seborrheic Keratoses, Molluscum, Papilloma (skin tags), Lentigines (age spots), Condyloma (genital warts), and Basal Cell Carcinoma (skin cancer).

EP 057 030 provides a hand-held device for the cryogenic treatment of a body, comprising a container for a cryogenic fluid and an application end, the container being in the form of an isothermal reservoir comprising at one of its ends a wide filler opening which can be sealed by a stopper while its other end has passing through it a channel or conduit for the flow of liquid, this other end being equipped with an adapted application nozzle, the sealing stopper of the reservoir being provided with a vent for the escape of the vaporised fraction of the cooling liquid and comprising, if appropriate, means for regulating the cross-section of this vent.

WO 2004/042763 provides an applicator for an anti-microbial solution and includes an aerosol container and an applicator pad assembly having a hollow arm. The hollow arm has a proximal end attached to an aerosol cap and a distal end having a flanged arm plate to receive a foam applicator pad. The aerosol cap is removably attached to the aerosol container. A solution flow control is in communication with the aerosol container for selectively dispensing the anti-microbial solution. The aerosol container holds the antimicrobial solution under pressure and flow is controlled by a pressure-sensitive flow control tab.

U.S. Pat. No. 6,226,996 provides a device that uniformly cools a surface to a specified temperature using a mist of cryogenic fluid. The device comprises a cryogenic fluid reservoir, a valve for controllably releasing the fluid through an atomizing nozzle, a non-contact temperature sensor, and a control unit to display the measured temperature. The control means can optionally pre-set the desired surface temperature and control the valve. The application of mist can be controlled. However, this device does not limit the area of application of the cryogenic fluid. Various cryogenic devices used in cryosurgical procedures have been known in the prior art. U.S. Pat. No. 5,224,943 discloses a cryosurgical probe comprising a slidable valve actuator member, wherein said actuator is urged by a spring to adopt a position.

The system disclosed in US '937 is suitable for delivery/application of cryogenic fluid using said probe.

U.S. Pat. No. 5,275,595 discloses a closed cycle cryosurgical instrument, equipped with several valves. The instrument is suitable for destroying a diseased or degenerated cells in a living being by freezing such cells without injury to the healthy body tissue. WO 2007/028975 discloses a mechanism and device for an application of cryogenic fluids for used in therapeutic treatments of the skin.

One device which has been used to assist the physician in providing localised refrigerant comprises an acrylic plate having frusto-conical apertures: the plate is placed upon a patients skin such that an aperture surrounds a lesion; the plate will typically have several apertures of varying sizes such that an appropriate amount of refrigerant can be placed upon a lesion without damaging skin surrounding a lesion. These plates are typically employed with liquid nitrogen, since, in some cases, accurate dispensing of such fluid from an aerosol canister filled with refrigerant can be problematic. One such type of acrylic plate device is marketed by Brymill Cryogenic Systems having a trade name "Cryoplate".

Whilst this type of device can assist in an improved localisation of refrigerant fluid and protection of adjacent skin areas, it is a relatively expensive item and needs to be subjected a sterilisation treatment after each use; furthermore this type of plastics can be easily scratched, limiting the number of times that the device can be used: scratched and/or otherwise damaged plates do not inspire any patient confidence. A further disadvantage is that the plate, once placed upon a patient's skin may be susceptible to leakage of a refrigerant fluid since the edges of the frusto-conical opening may not be maintained in continuous circumferential contact with the skin because of the contours of the body, patient movement and the fact that the lips of the frusto-conical aperture are coplanar with the underside of the planar acrylic member. Furthermore, the absence of a. handle on a material having non-textured surface may lead to slippage in use. A still further problem is that the device needs to be held down manually, whereby the physician's hand or the hand of his assistant/the patient is susceptible to intimate contact with cryogenic fluid in the event of a spillage. This application has neither been used nor advocated with aerosol based cryogenic products.

Cryotherapy by non-medically skilled personnel requires safe and easy-to-handle tools. To this end, WO 2016/178161 describes a pen for the treatment of dermatological disorders, such as warts and the like, by means of a coolant. The device is focused primarily on liquid dinitrogen oxide ($N_2O$) as a cooling medium. $N_2O$ is advantageous since it does not occur in a solid, non-fluid state during normal use of the pen. The pen comprises an applicator for the administration of the coolant to a dermatological surface, and a valve body comprising a coolant passage. The coolant passage is provided with at least one bypass for the coolant. WO '161 discloses a pen which pen comprises: a distal part comprising a holder for the storage of a coolant and a proximal part comprising an applicator for the administration of the coolant to the dermatological surface to treat, which parts extend axially and which parts are in coolant communication by means of a coolant passage in the proximal part, in which a valve body is provided for closing off and/or opening the passage, in which the passage is provided with at least one bypass for the coolant. The applicator of said device valve disclosed in WO '161 contains a ball that is resiliently bearing. The ball is configured to close off the part of the coolant passage proximally to the valve body. The resilient bearing of the ball means that the ball rests on a spring.

WO 2007/009282 discloses a spray device for dispensing a cooling fluid, which spray device comprises a reservoir in which the cooling fluid is stored in liquid form at an overpressure, a fluid outlet valve, and a spray head which has a capillary tube. The spray device comprises a capillary tube arranged in the spray head, there is also a further capillary tube (as riser tube) arranged in the reservoir. The inlet end of this capillary tube arranged in the reservoir extends into the cooling fluid stored in liquid form in the reservoir. The outlet end of the capillary tube is connected to the fluid outlet valve. Therefore, when the valve is actuated, an aerosol is already generated in the capillary tube, and this aerosol further evaporates and then passes through the fluid outlet valve.

In WO 2014/114696 a device comprising a container containing a refrigerant and having an outlet for the refrigerant and a valve communicating with the outlet, and an applicator mounted or mountable to the container is disclosed. The said applicator has an outer wall and forming a chamber at least when connected to the container. The device of WO '696 is equipped with a spring valve, which controls locked/unlocked position of the applicator. Said container containing a refrigerant, includes an outlet with a valve actuated by pressing and an applicator mounted on the container and connected to the outlet, wherein contact member is mounted and protruding from the applicator.

Wartie® Wart Remover is a commercially available OTC cryosurgery product to be used at home. Wartie® Wart Remover consists of i) pressurized canister filled with compressed liquid gas dimethyl ether (50 ml), ii) a custom application unit used to administer the cold delivered by the cryogen to the wart; iii) instructions for use.

However, above mentioned devices are not easy to handle with, so the use of such devices poses a risk for inappropriate application and destruction of healthy skin. Moreover, none of the above mentioned devices offers any sort of a signal or a notice to a user that device is in open position, i.e. "ready" for the application of a cryogenic fluid onto the diseased skin in a subject in need.

Given the disadvantages of current human epidermal and mucosal epidermal skin cooling techniques, a need exists for a device that provides a safe, easy-to-handle and economical alternative. The present invention aims to provide a device which employs carbon dioxide ($CO_2$) as a cooling medium.

There remains a need in the art for an improved applicator pen which will is easier to handle with and offers a safe application of a cryogenic fluid to wart tissue and/or diseased skin in a subject. Moreover, there remains a need for a cryogenic device of a design that can give an indication to user that said cryogenic device is activated, i.e. ready for the application onto the skin of the subject.

The present invention aims to resolve at least some of the problems mentioned above.

SUMMARY OF THE INVENTION

In a first aspect, the invention provides a device for the topical cryotherapy of dermatological disorders, such as warts, in a subject in need thereof, the device comprising:

- a housing for holding a pressurized carbon dioxide cartridge;
- an applicator nozzle comprising (i) an internal channel for guiding the outflow of carbon dioxide from said pressurized carbon dioxide cartridge, and (ii) an applicator surface onto which carbon dioxide ice may be formed and compacted as a dry ice pellet which then serves as the applicator tip of the device and which is held on the wart or the intended location of the skin;
- an actuator mechanism for controlling an outflow of carbon dioxide from said pressurized carbon dioxide cartridge to said applicator nozzle, which actuator mechanism is movable between a first, closed position and between a second, open position.

The inventors have thus realized a device which allows for the formation of a compressed dry ice pellet on the tip of the pen, i.e. the applicator surface which provides a contact surface for the applicator nozzle. The dry ice pellet on the tip of the applicator pen can then be usefully employed for the treatment of skin disorders by cold therapy.

In a second aspect, the present invention provides a kit for assembling a device for the topical cryotherapy of dermatological disorders, such as warts, in a subject in need thereof, the kit comprising:

- a housing for holding a pressurized carbon dioxide cartridge;
- an applicator nozzle comprising (i) an internal channel for guiding the outflow of carbon dioxide from said pressurized carbon dioxide cartridge, and (ii) an applicator surface onto which carbon dioxide ice may be formed;
- an actuator mechanism for controlling an outflow of carbon dioxide from said pressurized carbon dioxide cartridge to said applicator nozzle, which actuator mechanism is movable between a first, closed position and between a second, open position.

In another aspect, the present invention provides a cryogenic applicator pen comprising an actuator assembly for controlling an outflow of a cryogenic fluid, wherein said actuator assembly comprises at least one spring leaf (303), wherein said spring leaf (303) on one side bears against a ball (304) of a ball valve and on an opposite side bears against a positioning casing (302) bearing a needle (307) for piercing a cryogenic fluid cartridge.

The inventors achieved a cryogenic applicator pen comprising an actuator assembly for controlling an outflow of a cryogenic fluid, which applicator pen upon activation causes a haptic signal to an operator. Moreover, the cryogenic applicator pen is easier to be activated and used by an operator than the known devices, as only one-direction twist of a pen casing is possible.

In another aspect, the present invention relates to an actuator assembly suitable for cryogenic device for controlling an outflow of a cryogenic fluid, wherein said actuator assembly comprises at least one spring leaf (303) and a needle (307), whereby said spring leaf is bearing against a ball (304) of a ball valve and whereby said actuator assembly is sealed to said cryogenic device by sealing o-rings.

Said actuator assembly is suitable for different cryogenic fluids and provides the cleaner and safer use of such cryogenic pen to the subject in need.

In another aspect, the present invention provides for a method for the administration of the cryogenic applicator pen or the cryogenic device comprising the actuator assembly of the present invention, which method comprises:

- providing the pen and/or cryogenic device for the treatment of dermatological disorders;
- arming of said pen and/or cryogenic device with a cryogenic fluid cartridge onto the said actuator assembly of an applicator of said pen and/or device using a ring hook connecting means (105,108) to close an assembly (100.300);
- piercing of said cryogenic fluid cartridge (110) by a needle (307) secured onto the foot of a positioning casing (308) of the actuator assembly;
- flowing the cryogenic fluid under increased pressure from the cryogenic fluid cartridge (110) to the valve body (301, 302, 3030, 304, 305);
- exercising an external pressure onto the applicator end of the pen, which external pressure is exercised in opposite direction to the pressure exercised by the cryogenic fluid;
- flowing the cryogenic fluid past the valve body to the applicator nozzle (200);
- realizing the evaporative cooling at the applicator surface (201);
- removing the closing cap from the pen and/or cryogenic device.

A method according to an embodiment of the invention is particularly suitable for the use of such cryogenic application pen at home, as the applicator pen of the present invention represents a safer and user-friendlier applicator pen than the devices known in the prior art.

In a further aspect, the present invention provides a kit for assembling a device for the topical cryotherapy of dermatological disorders, such as warts, in a subject in need thereof, the kit comprising:

- a housing (100) for holding a cryogenic fluid cartridge (110);
- a cryogenic fluid cartridge (110);
- an applicator nozzle (200) comprising (i) an internal channel (202, 202') for guiding the outflow of cryogenic fluid from said cryogenic fluid cartridge (110), and (ii) an applicator surface (201) onto which cryogenic fluid ice may be formed;
- an actuator assembly suitable for cryogenic device, wherein said actuator assembly comprises at least one spring leaf (303) and a needle (307), whereby said spring leaf (303) is bearing against a ball (304) of a ball valve for controlling an outflow of cryogenic fluid from said cryogenic fluid cartridge (110) to said applicator nozzle (200), which actuator assembly (300) is movable between a first, closed position and between a second, open position.

DETAILED DESCRIPTION OF THE INVENTION

Figure 1:
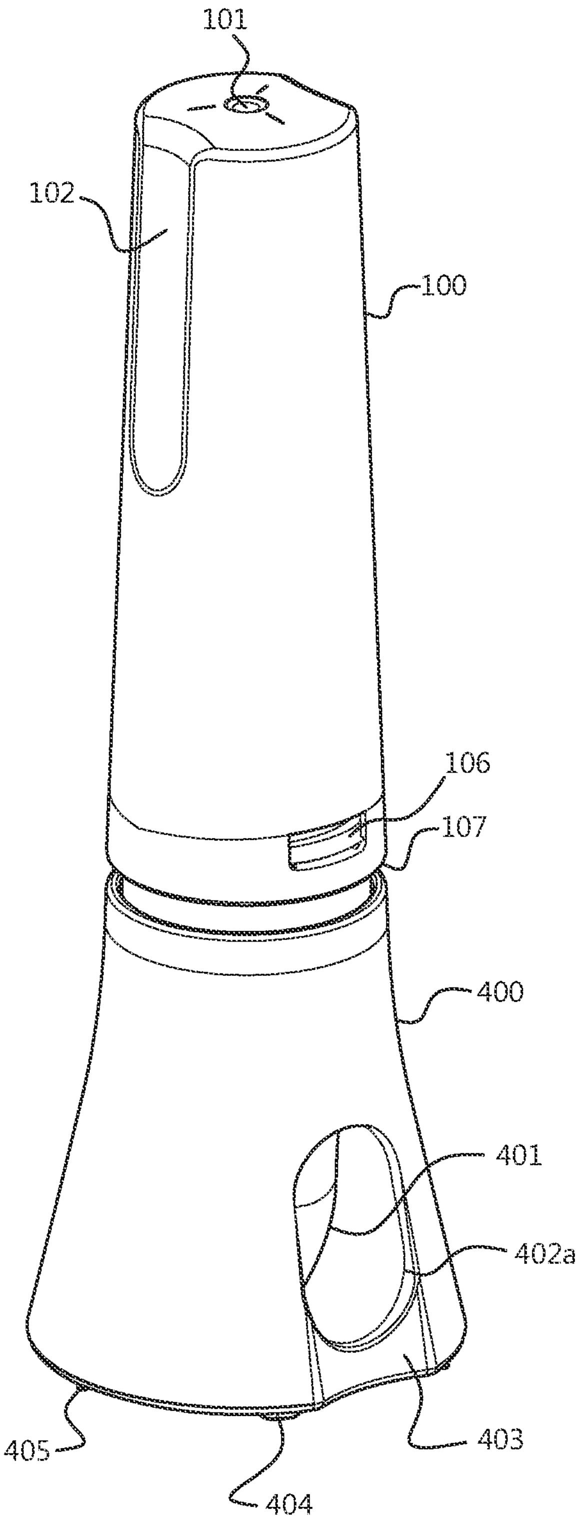
FIG. 1 shows schematically a perspective view of the device for the topical cryotherapy of dermatological disorders, such as warts, in a subject in need thereof.

The present invention concerns a cryogenic applicator pen comprising an actuator assembly for controlling an outflow of a cryogenic fluid, an actuator assembly suitable for cryogenic device for controlling an outflow of the cryogenic fluid, a method for the administration of the cryogenic applicator pen, and a kit for assembling a device for the topical cryotherapy of dermatological disorders.

In another aspect, the present invention concerns pen for forming carbon dioxide tablets.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent" or "wt. %", here and throughout the description unless otherwise defined, refers to the relative weight of the respective component based on the overall weight of the formulation.

The terms "actuator mechanism" and "actuator assembly", as used herein, are synonyms and mean a component of a cryogenic device or a cryogenic pen that is responsible for moving and controlling a mechanism or system, in this particular case dispensing the cryogenic fluid, preferably carbon dioxide by opening a valve.

The terms "pen" and "device" as used herein, are synonyms and mean an object which is used for application of the cryogenic fluid for treatment of skin disorders.

Device for Topical Cryotherapy

In a first aspect, the invention provides a device for the topical cryotherapy of dermatological disorders, such as warts, in a subject in need thereof, the device comprising:

- a housing for holding a pressurized carbon dioxide cartridge;
- an applicator nozzle comprising (i) an internal channel for guiding the outflow of carbon dioxide from said pressurized carbon dioxide cartridge, and (ii) an applicator surface onto which carbon dioxide ice may be formed and compressed;
- an actuator mechanism for controlling an outflow of carbon dioxide from said pressurized carbon dioxide cartridge to said applicator nozzle, which actuator mechanism is movable between a first, closed position and between a second, open position.

The inventors have thus realized a device which allows for the formation of compressed dry ice pellets on the tip of the pen, i.e. the applicator surface which provides a contact surface for the applicator nozzle. The dry ice pellet on the tip of the applicator pen can then be held against the wart or other skin disorder, or the desired location of skin treatment.

The dry ice pellet will be formed upon contact of compressed carbon dioxide with any type of material. The carbon dioxide will freeze and form carbonic snow or dry ice. Although other methods are contemplated by the inventors, a simple cloth or even direct application of the carbon dioxide outflow on the skin would create dry ice or carbonic snow. However, for a dry ice pellet of sufficient durability, the dry ice needs to be compacted under some force. To this effect, the nozzle needs to be pressed against a counter surface such as the closing cap proposed in a preferred embodiment Upon skin contact the dry ice or carbonic snow will extract heat for its sublimation from the treated skin surface. The extraction of heat from the skin will effectively lower the temperature of the treated skin, and accordingly provide the cryotherapy. The inventors have envisioned that a device can be provided which forms a predetermined amount of dry ice to arrive at a sufficient cooling of the skin tissue without causing injuries to the skin. Moreover, after formation of the ice pellet, any excess of carbon dioxide fluid will be vented away from the skin and this also contributes to the safety of the device with respect to skin damage.

In a preferred embodiment, the present invention provides a device according to the first aspect of the invention, further comprising a closing cap, detachably provided across from said applicator nozzle, said closing cap comprising a cup which, in an arranged position, faces towards said applicator nozzle, thereby forming a sublimation chamber between said cup of said closing cap and said applicator nozzle; whereby said cup is configured for obstructing the outflow of carbon dioxide gas from said applicator nozzle, thereby forming solid carbon dioxide crystals and compacting the crystals to a sufficiently durable pellet within said sublimation chamber The device as described above provides, upon actuation by a user, a restricted outflow of pressurized carbon dioxide from the applicator nozzle. The device is configured to provide the least turbulent flow of carbon dioxide within the internal channel of the applicator nozzle as violent turbulence will damage the pellet formation. Upon entering the sublimation chamber, the carbon dioxide gas flow is obstructed by the cup. At atmospheric pressure, sublimation/deposition occurs at −78.5° C. (−109.3° F.) or 194.65 K. During deposition of carbon dioxide, the solid carbon dioxide crystals accumulate in the sublimation chamber. Upon continued actuation of the device a sufficient amount of carbon dioxide crystals are formed which are compressed to a carbon dioxide pellet or tablet. The carbon dioxide pellet is sufficiently durable to be used, attached on the device or loosely dispensed from the device, for cool treatment of skin tissue, amongst other.

Figure 9A:
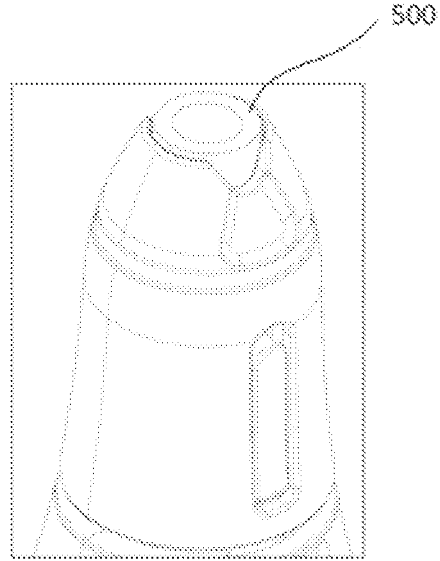
FIG. 9A shows a perspective view of the applicator surface with the adhesion surface ring.
Figure 9B:
FIG. 9B shows a perspective view of the applicator surface without the adhesion surface ring.
Figure 9C:
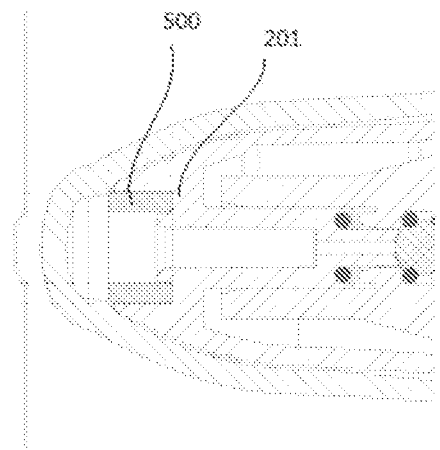
FIG. 9C and FIG. 9D show schematically a cross-sectional view in the longitudinal direction of a device according to the invention comprising the adhesion surface ring.

In a particularly preferred embodiment, the applicator additionally comprises an adhesion surface ring (500) on the top part of the applicator and depicted in FIGS. 9A, 9B and 9C. Said adhesion surface ring is made of thermoplastic polymeric material, preferably ultra-high-molecular-weight polyethylene (UHMW-PE), preferably sintered UHMW-PE. Said additional adhesion surface ring is used to provide an improved control of the turbulence during $CO_2$ expansion and to assist in adhering the formed carbon dioxide tablet to the applicator tip. The said adhesion surface ring is rough, gas permeable and it is inserted in the front of our device (=stem) as surface for the carbonic ice tablet to form and stick. It has been unexpectedly found that implementation of this adhesion surface ring ensures optimal ice-anchor formation between the carbonic ice tablet and the countless pores of the ring. Therefore, said adhesion surface ring improves overall adhesion between the carbonic ice tablet and the applicator surface of the device of the invention.

In a further preferred embodiment, UHMW-PE is used as a material to make the adhesion surface ring. UHMW-PE is a linear polyethylene that differs from PE standard grades in its very high degree of polymerization. The combination of its excellent properties (e.g. outstanding abrasion resistance, chemical resistance, superior impact resistance and excellent mechanical properties), even in cryogenic conditions, makes this material particularly suitable for the present cryogenic pen. UHMW-PE is an extremely high viscosity polymer that is produced in the form of a powder and has an average particle size diameter typically ranging from 100-200 microns. As a result of its viscosity, it generally cannot be processed by the common methods used for ordinary thermoplastics. For the particular application, a “free sintering process” is used to produce porous parts such as filters, wicking parts and fluid delivery components.

In the preferred embodiment, the adhesion surface ring is made of UHMW-PE, which contributes to an exceptionally high notched impact strength, high energy absorption capacity at high stress rate, excellent wear-resistant properties, low coefficient of friction, very high chemical resistance to acids, alkalis and corrosive gases, highly resistant to environmental stress cracking, wide service temperature range from −200° C. to 90° C.

In a preferred embodiment, the present invention provides a device according to the first aspect of the invention, wherein the applicator surface of said applicator nozzle has a different surface roughness than the contact surface of said cup. Said surface roughness can be determined according to ISO 25178.

By providing a difference in surface roughness, the carbon dioxide dry ice tablet adheres to the applicator surface or the cup with the highest surface roughness upon disengagement of the applicator nozzle and the closing cap. By doing so, the carbon dioxide tablet can easily be manipulated on top of either the applicator nozzle or within the cup of the closing cap. This allows for forming a tablet with optimal mechanical properties and for ease of handling during the treatment of the subject.

In a preferred embodiment, the present invention provides a device according to the first aspect of the invention, wherein the applicator surface of said applicator nozzle has a greater surface roughness than the contact surface of said cup. Said surface roughness can be determined according to ISO 25178. It is preferred that the dry ice tablet is formed on top of the applicator nozzle. The applicator nozzle is by preference provided within the housing which also comprises the pressurized carbon dioxide cartridge. Carbon dioxide cartridge are generally cylindrically shaped and thus provide a pen-like form which is easy to handle and allows for an accurate treatment of the skin tissue.

In a preferred embodiment, the present invention provides a device according to the first aspect of the invention, wherein the applicator surface of said applicator nozzle has a surface roughness Ra greater than 250 μm, preferably higher than 300 μm, higher than 350 μm, higher than 400 μm, higher than 500 μm, higher than 600 μm, higher than 700 μm, higher than 800 μm, higher than 900 μm, or even higher than 1000 μm. The applicator surface of said applicator nozzle has a surface roughness Ra smaller than 2.5 mm and more preferably smaller than 1.5 mm. Said surface roughness can be determined according to ISO 25178. A sufficiently high surface roughness of the applicator surface allows for very good adherence of the carbon dioxide tablet to the applicator surface.

In a preferred embodiment, the present invention provides a device according to the first aspect of the invention, wherein the contact surface of said cup has a surface roughness Ra not greater than 250 μm. Said surface roughness can be determined according to ISO 25178. Accordingly, said cup of closing cap has a smooth surface which does not adhere to the formed carbon dioxide tablet and thereby easily releases the carbon dioxide tablet upon disengagement of the closing cap and the applicator nozzle after formation of the carbon dioxide tablet.

In a preferred embodiment, the present invention provides a device according to the first aspect of the invention, wherein the applicator surface of said applicator nozzle is greater than the contact surface of said cup. For the same reasons as described above, a higher applicator surface allows for better adhesion of the dry ice tablet relative to the cup having a smooth and smaller surface.

In a further preferred embodiment, the cryogenic applicator pen further comprises:

a housing for holding a cryogenic fluid cartridge;

an applicator nozzle comprising (i) an internal channel for guiding the outflow of cryogenic fluid from said cryogenic fluid cartridge, and (ii) an applicator surface onto which cryogenic fluid ice may be formed.

Cryogenic fluid cartridges are provided for containing a cryogenic fluid coolant under increased pressure. Therefore, a cryogenic fluid cartridge constitutes in closed position a closed volume in which the coolant can be stored. The cryogenic fluid cartridge preferably contains an opening that, in unused condition of the cryogenic fluid cartridge, is closed off by a closure, which closure serves to keep the coolant within the cryogenic fluid cartridge in unused condition. A coolant comprises one or more chemical agents. A coolant appropriate for use in the present invention can deliver temperatures that are sufficiently low for the treatment of warts. Dimethyl ether, n-butane, isobutene, propane, nitrogen, $N_2O$ and/or halogenated hydrocarbons such as, for example, tetrafluormethane, trifluormethane and 1,1,1,2-tetrafluorethane are examples of chemical agents that are appropriate for use as components of a cryogenic fluid that is suitable for the present invention. A skilled worker will understand that a cryogenic fluid coolant can consist of several different chemical agents in order to decrease the internal pressure of the cryogenic fluid cartridge necessary for achieving a desired boiling point. A skilled worker will also understand that because of the high internal pressure that is present in the holder, a cryogenic fluid coolant can be present in the form of a liquid or a gas/liquid mixture. For coolants in the form of a liquid, the term liquid coolant is used in this text. For coolants in the form of a gas, the term gaseous coolant is used in this text. Several materials, such as for example steel and aluminium, are appropriate as a material for the holder.

Several materials, such as for example steel, rubber, plastic and/or a synthetic material are appropriate as a material for the closure of the cryogenic fluid cartridge. A skilled worker will understand that the type of material for the cryogenic fluid cartridge and the closure of the cryogenic fluid cartridge can be chosen depending on the resistance to corrosion as a result of contact with the cryogenic fluid coolant, and the possibility to resist the high internal pressure levels and the low temperatures when enclosing a cryogenic fluid, such as, for example, liquid dinitrogen oxide under increased pressure. In the wart pen according to the present invention, the gas cartridge is at least partially located in a specially designed cartridge housing. Several materials, such as for example steel and aluminium, are appropriate as a material for the cryogenic fluid cartridge. The cartridge preferably forms a closed volume.

Upon actuation, the needle pierces the cryogenic fluid cartridge and a cryogenic fluid moves towards the applicator nozzle of said pen. Several materials, such as for example steel, rubber, plastic and/or a synthetic material are appropriate as a material for part of the cartridge that is pierced. A skilled worker will understand that the type of material for the cartridge and the part of the cartridge which is pierced can be chosen depending on the resistance to corrosion as a result of contact with the coolant, and the possibility to resist the high internal pressure levels and the low temperatures when enclosing a coolant, such as, for example, liquid dinitrogen oxide under increased pressure.

Applicator Nozzle

According to the first aspect, the present invention provides a cryogenic applicator pen, comprising an applicator nozzle for administration of the cryogenic fluid at the dermatological area to treat. In a preferred embodiment, at least a part of the said applicator nozzle, such as the applicator surface, is preferably exposed to the environment. At administration, liquid coolant will evaporate at the applicator surface so that the applicator nozzle is cooled down to low temperatures and the cooled-down applicator nozzle will be brought into contact with the dermatological area to treat. The applicator nozzle and a cryogenic fluid cartridge of the pen are in coolant communication with each other by means of a cryogenic fluid passage. The cryogenic fluid passage is defined as a preferably axially extending opening in the applicator part of the pen in which flow of the cryogenic fluid is possible. Cryogenic fluid communication means that, at the connection of the applicator nozzle and a cryogenic fluid cartridge, these parts are connected to each other so that cryogenic fluid from the cartridge can flow to the cryogenic fluid passage. In the cryogenic passage, an actuator assembly is provided for closing off and/or opening the cryogenic fluid passage. When closing cryogenic fluid passage by means of the valve body, the valve body constitutes a barrier for the cryogenic fluid so that the cryogenic fluid cannot flow to the applicator. When opening the cryogenic fluid passage, the barrier for the cryogenic fluid by means of the valve body is raised and the cryogenic fluid can flow to the applicator nozzle. The cryogenic applicator pen according to the present invention preferably relates to a compact pen, especially for home use, that is compact, easy and safe to use, can deliver efficient evaporative cooling, has a low cost price and is disposable.

In a preferred embodiment, the applicator nozzle of said applicator pen contains an applicator surface and the pores of average pore size decreasing in the axial direction to the administration surface.

Decrease of the average pore size of the applicator nozzle in the direction of the administration surface provides sufficient room for removing the gas that has been generated during evaporative cooling, resulting in an increased storage of cold.

The cryogenic applicator pen according to the present invention is appropriate for the treatment of warts by the low temperatures, preferably lower than −65° C., more preferably lower than −70° C. and most preferably lower than −95° C., that can be reached at the applicator surface of the said pen. These low temperatures are generated when a cryogenic fluid, with a low boiling point, preferably lower than 10° C., more preferably lower than 0° C., still more preferably lower than 50° C. and most preferably lower than −85° C., evaporates quickly at the applicator surface at environment temperature or at the body temperature of a human body. The heat required for the evaporation of the cryogenic fluid is withdrawn from the applicator surface, so that this applicator surface cools down to low temperatures. In other words, the applicator surface is cooled down to low temperatures by means of evaporative cooling. The use of an applicator surface cooled down to a low temperature at one or more warts causes the destruction of the one or more warts by killing the cells. The obtained evaporative cooling reaches temperatures that are sufficiently low for the treatment of warts, preferably a temperature lower than −60° C., more preferably a temperature lower than −70° C. and most preferably a temperature lower than −75° C., without causing hypothermia and/or without undesired interaction of the low temperatures with areas that do not require treatment, such as, for example, healthy skin tissue surrounding the wart. Several other dermatological disorders than warts such as for example hyperpigmentation and fibroma, can also be treated by using the obtained evaporative cooling.

In a preferred embodiment, the present invention provides a cryogenic applicator pen according to the first aspect of the invention, wherein the applicator surface of said applicator nozzle is provided with a multitude of protrusions and/or recessions. Said protrusions and/or recessions aid to enhancing the applicator surface area, thereby facilitating the contact of the cryogenic fluid with a skin surface of a subject in need.

In a preferred embodiment, the present invention provides a cryogenic applicator pen according to the first aspect of the invention, wherein said applicator nozzle is provided from a porous material or encloses a porous structure that improves the attachment of the cryogenic fluid and/or cryogenic fluid ice to the applicator nozzle. A porous material is preferably used for ensuring a higher contact surface area.

In a preferred embodiment, the present invention provides a cryogenic applicator pen according to the first aspect of the invention, wherein said applicator nozzle has a porous structure and is preferably constituted of a material with a high thermal conductivity and is configured to spread cryogenic fluid while the said cryogenic fluid withdraws heat from the applicator for evaporation of cryogenic fluid. Sintered metals, such as for example sintered copper, aluminium or steel can also be used as material for the applicator. Moreover, the applicator can also partially or in whole be fabricated of a porous synthetic material such as, for example, porous polyethylene. The applicator comprises an administration surface, by which low temperatures can be administered to one or more warts to treat. The applicator surface preferably corresponds to the side of the applicator nozzle that is most distally located with respect to the cryogenic fluid cartridge. The part of the applicator nozzle not located at the applicator surface is preferably protected from the environment. The applicator nozzle can have a porosity of 10% to 95%. The applicator nozzle preferably has a porosity of 20% to 70%, and more preferably of 35% to 65%. The applicator nozzle can have an average pore size of 1 μm to 350 μm. The applicator nozzle preferably has an average pore size of 1 μm to 750 μm, more preferably of 10 μm to 650 μm, even more preferably 20 to 500 μm and most preferably 150 to 250 μm.

Decrease of the average pore size of the applicator nozzle, in the axial direction of the applicator to the applicator surface, results in a higher storage of cold. In other words, the decrease of the average pore size provides a concentration of cold in the direction of the applicator surface, allowing a more efficient use of the evaporative cooling. The decrease of the average pore size, in the axial direction of the applicator to the administration surface, should be seen as a decrease of the average pore size per transversal or perpendicular surface with respect to the axial direction.

According to another preferred embodiment of the cryogenic applicator pen, the average pore size of the applicator nozzle, in the axial direction to the administration surface, decreases from 60-350 μm to 1-55 μm. The average pore size of the applicator nozzle, in the axial direction to the administration surface, preferably decreases from 60-250 μm to 1-50 μm, and more preferably from 65-150 μm to 10-50 μm. Along the axial direction of the applicator nozzle, the porosity of the applicator, in which the porosity is considered per transversal or perpendicular surface with respect to the axial direction, can have a variation of at most 30%. This variation of the porosity preferably amounts to at most 20% and more preferably at most 15%. Combined with this variation of the porosity of at most 30%, preferably at most 20% and most preferably at most 15%, the average pore size of the applicator nozzle, in the axial direction of the administration surface, preferably decreases from 60-350 μm to 1-55 μm. Combined with this variation of the porosity of at most 30%, preferably at most 20% and most preferably at most 15%, the average pore size of the applicator nozzle, in the axial direction of the administration surface, more preferably decreases from 60-250 μm to 1-50 μm. Combined with this variation of the porosity of at most 30%, preferably at most 20% and most preferably at most 15%, the average pore size of the applicator nozzle, in the axial direction of the applicator surface, still more preferably decreases from 65-150 μm to 10-50 μm.

According to another preferred embodiment, said applicator nozzle contains a transformable foam, more preferably a transformable foam with an open cell structure. The material of said foam is preferably polyurethane (PU) and more preferably a polyester polyurethane. The hardness of said foam is preferably 4 to 30 kPa, more preferably 5 to 25 kPa, still more preferably 6 to 20 kPa, even more preferably 7 to 15 kPa and most preferably 8 to 10 kPa. The advantage is that the applicator surface deforms when it is pushed against the wart. As a result, the contact surface between the applicator and the wart increases and an efficient heat transfer can occur and the larger part of the wart is exposed to the generated cold in the applicator nozzle. Further, a pressure is applied during the application of the applicator surface to the wart so that the pores of the foam adjacent the applicator tip or the administration surface, first and foremost melt, and then be at least partially compressed. This hampers the flow of the coolant in this zone, resulting in a greater Joule-Thomson effect, causing the cooling effect in this zone to be larger. The pores further away from the applicator or the applicator surface stay frozen for longer and maintain their dimensions during use. Preferably, the dimensions of the pores adjacent the applicator tip or the applicator surface will be compressed during the application of the applicator on the wart by 20 to 80%, more preferably by 30 to 70%, still more preferably by 40 to 60% and most preferably by 50%.

In a preferred embodiment, said foam is comprising pores having a pore size of 100 μm to 1000 μm, more preferably from 200 to 900 μm, still more preferably 300 to 800 μm, even more preferably from 400 to 700 μm and most preferably from 450 to 650 microns. Such a pore size ensures that the flow of the coolant is hampered enough in order to obtain the desired cooling effect, but also does not lower the speed of the flow too much.

In a preferred embodiment, said applicator surface has a density of 19 to 67 kg/m3, preferably of 24 to 62 kg/m3, more preferably of 29 to 57 kg/m3, still more preferably of 34 to 52 kg/m3 and most preferably of 39 to 47 kg/m3. This ensures that coolant flows quickly through the applicator, thus allowing to obtain a low temperature.

In a preferred embodiment, said applicator surface has a maximum diameter of at last 3 mm, preferably at least 4 mm, more preferably at least 5 mm; most preferably at least 6 mm and at most 10 mm, preferably at most 9 mm, more preferably at most 8 mm and most preferably at most 7 mm. Such a diameter provides a sufficiently large contact surface between the applicator and the wart.

According to an embodiment of the first aspect of the invention, the applicator nozzle has a volume of between 0.05 $cm^3$ to 1.00 $cm^3$. The applicator nozzle preferably has a volume of at least 0.150 $cm^3$ and preferably at most 0.500 cm3. The applicator nozzle can occur in several geometries. The applicator nozzle can thus amongst other things have the shape of a bar, cube or cylinder. The applicator nozzle preferably has the shape of a cylinder. Said volumes and geometries are appropriate for obtaining an applicator nozzle with an applicator surface that desirably is dimensioned for treating one or more warts. Moreover, said volumes are sufficiently large for allowing a sufficient degree of evaporative cooling to occur in the applicator nozzle by means of a cryogenic fluid.

In a preferred embodiment, the applicator comprises an applicator nozzle comprising a surface having e.g. a surface or contact area in the range of 0.01-4.0 $cm^2$, such as 0.1-2.5 $cm^2$.

The applicator nozzle, the actuator stem and/or said spring are preferably comprised of a polymer material. Good polymer materials for the applicator nozzle, the actuator stem and/or said spring may be, independently, selected from the group consisting of chlorinated polyvinyl chloride (CPVC), ethylene chlorotrifluoroethylene (ECTFE), (enhanced) polytetrafluoroethylene, (enhanced PTFE), high-density poly ethylene (HDPE), polyether ether ketone (PEEK), polypropylene (PP), polysulfone (PSU), polyphenylene sulfide (PPS), polyvinyl chloride (especially type 1 (PVC, Type 1) or type 2 (PVC, Type 2)), polyvinylidene fluoride (PVDF), polytetrafluoroethylene (PTFE), Polyamide-imide (PAI), ultra-high molecular weight polyethylene (UHMW) and also coated. Yet in a further embodiment, good materials for the applicator nozzle, the actuator stem and/or said spring may independently be selected from the group consisting of high-density poly ethylene (HDPE), low-density poly ethylene (LDPE), polyamide (PA), polycarbonate (PC), polyethylene terephthalate (PET) (including e.g. polyethylene terephthalate glycol PETG), polymethylpentene (PMP), polyoxymethylene (POM), polypropylene (PP), polystyrene (PS), polysulfone (PSU), polyvinyl chloride (especially rigid (PVC HART) and flexible (PVC WEICH), styrene acrylonitrile (SAN), ethylene chlorotrifluoroethylene (ECTFE), ethylene chlorotrifluoroethylene (ETFE), fluorinated ethylene propylene (FEP), polytetrafluoroethylene (PTFE), polyvinylidene fluoride (PVDF), ethylene propylene diene rubber (EPDM), fluorocarbon rubber (FPM), and acrylonitrile (nitrile) butadiene rubber (NBR).

In a preferred embodiment, the medicament device further comprises a removable closing cap for protecting the applicator nozzle. The cap can be placed over the nozzle preventing damage to the nozzle or the accidental actuation of the actuator mechanism.

Distally to the applicator nozzle, the actuator assembly comprises a needle, preferably a flat needle, that is preferably secured within a foot of a spring leaf positioning casing of said actuator assembly, and which needle is arranged to pierce the cryogenic fluid cartridge. Puncturing of the cryogenic fluid cartridge by means of the needle is preferably used for putting at disposal the cryogenic fluid, from the cryogenic fluid cartridge. The specific design of the actuator assembly positioning casing and the spring leaf reduce the clogging of the needle by iron particles, which is the common problem with the prior art devices. The clogging of the needle leads to problems of dispensing the cryogenic fluid from the cartridge and unreliable dosing. The above-mentioned problems are solved by the actuator mechanism of the invention.

The needle preferably consist of a material that is resistant to corrosion by contact with the cryogenic fluid and that can resist to increased pressure levels exercised by the cryogenic fluid as well as the low temperatures of the cryogenic fluid. In addition, the needle preferably consists of a material that can pierce the cryogenic fluid cartridge. For example, the needle is made of metal. The needle is preferably hollow so that the cryogenic fluid can flow through the said needle.

In a preferred embodiment, the present invention provides a cryogenic applicator pen according to the first aspect of the invention, further comprising at least one, preferably two or more, venting holes within the applicator surface and/or within the internal channel for conducting the cryogenic fluid to the applicator nozzle. Said cryogenic applicator pen may comprise between 1 and 12 venting holes, preferably between 1 and 8 venting holes and more preferably between 1 and 4 venting holes, such as one venting hole, two, three or four venting holes. More preferably said device is provided with two or three venting holes, and most preferably said device has two venting holes. Preferably, said venting holes are provided symmetrically around the longitudinal axis of said internal channel and the passage. Also, said venting holes preferably extend outwardly. Also preferably, said venting holes are provided perpendicularly or diagonally to a longitudinal axis of said internal channel. Also, said venting holes are preferably provided upstream of said applicator surface.

In a preferred embodiment, the present invention provides a cryogenic applicator pen according to the first aspect of the invention without venting holes in the nozzle but with an alternative venting path longitudinally, diagonally or radially along the cap or along the walls of the actuator mechanism that allows degassing of excess cryogenic fluid. Such venting paths communicate with the open air and guarantee the steady flow of the cryogenic fluid within said applicator nozzle.

Venting holes and venting paths may be provided within the cup, within the applicator surface, or preferably within the internal channel within the applicator nozzle. The venting holes and venting paths provide a safety mechanism once the cryogenic fluid reaches the surface of the applicator. The cryogenic fluid reaches the surface of the applicator, and the outflow of the cryogenic fluid continues, the excess of the cryogenic fluid can easily be ventilated through the ventilation holes and do not interfere with the cryogenic fluid of the top of the applicator. Upon exit of cryogenic fluid snow through the venting holes, the user will easily recognize and stop the actuation of the device. In addition, provision of venting holes, especially when provided within the internal channel within the applicator nozzle, allows for a good laminar flow of the cryogenic fluid through the nozzle and thus prevents premature formation of the cryogenic fluid crystals within the nozzle.

In a preferred embodiment, the present invention provides a device according to the first aspect of the invention, wherein said internal channel within said applicator nozzle is provided with at least one, preferably two, venting holes, upstream of said applicator surface.

In a preferred embodiment, the present invention provides a device according to the first aspect of the invention, wherein said internal channel within said applicator nozzle is provided with at least one, preferably two, venting holes, which venting holes extend outwardly. By providing venting holes which extend outwardly, excess cryogenic gas, which is produced during the process of evaporative cooling, can easily escape and thereby offer a visual control to the user and safer application of said pen.

In a preferred embodiment, the present invention provides a device according to the first aspect of the invention, wherein said internal channel within said applicator nozzle is provided with at least one, preferably two, venting holes, which venting holes are provided perpendicularly to a longitudinal axis of said internal channel.

In a preferred embodiment, the present invention provides a device according to the first aspect of the invention, wherein said internal channel within said applicator nozzle is provided with two venting holes, which venting holes are preferably provided across from each other on opposite sides of said internal channel.

The applicator nozzle allows the treatment of the disorder by topical local contact of the applicator surface on the nail or skin. This is safer and also more effective than applicators that need contact with a larger region than lesion or applicators that serve more than the lesion. The applicator may especially be configured to provide the cryogenic fluid on the surface of the applicator to treat a local topical area of ranging from 0.01-4 $cm^2$, such as 0.02-2.5 $cm^2$, such as 0.1-1.0 $cm^2$, like 0.1-0.5 $cm^2$, by means of a topical, direct contact. Hence, in an embodiment, the applicator nozzle comprises a surface having a surface area or contact area in the range of 0.01-4 $cm^2$, preferably 0.1-2.5 $cm^2$.

In a preferred embodiment, the present invention provides a device according to the first aspect of the invention, wherein said applicator surface is formed by a multitude of axially extending fins. Such fins ensure the provision of a higher applicator surface of the applicator nozzle and thus contribute to the retention of the carbon dioxide tablet to the applicator nozzle. In a more preferred embodiment, the present invention provides a device according to the first aspect of the invention, wherein said axially extending fins having a rectangular cross-section.

In an even more preferred embodiment, the present invention provides a device according to the first aspect of the invention, wherein said multitude of axially extending fins is provided with a cylindrically surrounding rim. The cylindrically surrounding rim aids to the holding of the carbon dioxide tablet onto the surface of the applicator nozzle.

In a preferred embodiment, the present invention provides a device according to the first aspect of the invention, wherein said internal channel of said applicator nozzle is provided with a cylindrically surrounding internal wall. The cylindrically surrounding internal wall aids to the maintenance of a laminar flow of the carbon dioxide gas within the internal channel of the applicator nozzle. A laminar flow of carbon dioxide within the applicator nozzle is important for preventing the undisturbed, least turbulent formation of carbon dioxide crystals within the applicator nozzle. In a preferred embodiment, the present invention provides a device according to the first aspect of the invention, wherein said internal channel of said applicator nozzle is designed to allow for a laminar flow of carbon dioxide gas through said applicator nozzle.

In a more preferred embodiment, the present invention provides a device according to the first aspect of the invention, wherein said surrounding internal wall of said internal channel extends downstream of said applicator surface. Accordingly, a cylindrically surrounding internal rim is formed, which surrounding rim aids to the holding of the carbon dioxide tablet onto the surface of the applicator nozzle. The surrounding rims or walls may be cylindrical, cubical, conical or take any three-dimensional volume that accumulates dry ice.

In a preferred embodiment, the present invention provides a device according to the first aspect of the invention, wherein the applicator surface of said applicator nozzle is provided with a multitude of protrusions and/or recessions. Said protrusions and/or recessions aid to enhancing the applicator surface area, and thereby aid to holding the formed carbon dioxide tablet onto the applicator surface.

In a preferred embodiment, the present invention provides a device according to the first aspect of the invention, wherein said applicator nozzle is provided from a porous material or encloses a porous structure that improves the attachment of the dry ice to the applicator nozzle. A porous material is preferably used for ensuring a higher contact surface area and thus is especially suited for holding the carbon dioxide tablet onto the surface of the applicator nozzle.

In a preferred embodiment, the present invention provides a device according to the first aspect of the invention, further comprising at least one, preferably two or more, venting holes within said applicator surface and/or within said internal channel. Said device may comprise between 1 and 12 venting holes, preferably between 1 and 8 venting holes and more preferably between 1 and 4 venting holes, such as one venting hole, two, three or four venting holes. More preferably said device is provided with two or three venting holes, and most preferably said device has two venting holes. Preferably, said venting holes are provided symmetrically around the longitudinal axis of said internal channel and the passage. Also, said venting holes preferably extend outwardly. Also preferably, said venting holes are provided perpendicularly or diagonally to a longitudinal axis of said internal channel. Also, said venting holes are preferably provided upstream of said applicator surface.

In a preferred embodiment, the present invention provides a device according to the first aspect of the invention without venting holes in the nozzle but with an alternative venting path longitudinally, diagonally or radially along the cap or along the walls of the actuator mechanism that allows degassing of excess carbon dioxide. Such venting paths communicate with the open air and guarantee the steady flow of carbon dioxide gas within said applicator.

Venting holes and venting paths may be provided within the cup, within the applicator surface, or preferably within the internal channel within the applicator nozzle. The venting holes and venting paths provide a safety mechanism once the carbon dioxide tablet is formed. When a full carbon dioxide tablet is formed, and the outflow of carbon dioxide gas continues, the excess of carbon dioxide can easily be ventilated through the ventilation holes and do not interfere with the formed carbon dioxide tablet. Upon exit of carbon dioxide snow through the venting holes, the user will easily recognize and stop the actuation of the device. In addition, provision of venting holes, especially when provided within the internal channel within the applicator nozzle, allows for a good laminar flow of carbon dioxide gas through the nozzle and thus prevents premature formation of carbon dioxide crystals within the nozzle.

In a preferred embodiment, the present invention provides a device according to the first aspect of the invention, wherein said internal channel within said applicator nozzle is provided with at least one, preferably two, venting holes, upstream of said applicator surface.

In a preferred embodiment, the present invention provides a device according to the first aspect of the invention, wherein said internal channel within said applicator nozzle is provided with at least one, preferably two, venting holes, which venting holes extend outwardly. By providing venting holes which extend outwardly, excess carbon dioxide gas can easily escape and thereby offer a visual control to the user.

In a preferred embodiment, the present invention provides a device according to the first aspect of the invention, wherein said internal channel within said applicator nozzle is provided with at least one, preferably two, venting holes, which venting holes are provided perpendicularly to a longitudinal axis of said internal channel.

In a preferred embodiment, the present invention provides a device according to the first aspect of the invention, wherein said internal channel within said applicator nozzle is provided with two venting holes, which venting holes are preferably provided across from each other on opposite sides of said internal channel.

In a preferred embodiment, the present invention provides a cryogenic applicator pen according to the first aspect of the invention, further comprising a removable closing cap for closing an applicator nozzle. Said cap is detachably provided across said applicator nozzle, said closing cap comprising a cup which, in an arranged position, faces towards said applicator nozzle, thereby forming a sublimation chamber between said cup of said closing cap and said applicator nozzle; whereby said cup is configured for obstructing the outflow of the cryogenic fluid.

In a preferred embodiment, the removable closing cap is preferably arranged to enclose the applicator nozzle in a fluid-tight manner. The term "fluid-tight" in this text means that there is a minimum leakage of the cryogenic fluid, in the case this cryogenic fluid is present in the applicator nozzle. The term "minimum leakage" in this text means that maximum 5% of the cryogenic fluid is released to the environment, when the removable closing cap is attached to the proximal side of the cryogenic applicator pen. In a further preferred embodiment, maximum 0.3%, more preferably maximum 1.0% and most preferably maximum 0.1% of the cryogenic fluid is released to the environment, when the removable closing cap is attached to applicator nozzle of the cryogenic applicator pen. The minimizing of the release or loss of the cryogenic fluid to the environment, at the applicator nozzle, ensures that the cryogenic fluid can be optimally used for cooling down the applicator nozzle by means of evaporative cooling. When cryogenic fluid is present at the applicator nozzle, the removable closing cap moreover provides an isolation of the applicator nozzle with respect to the environment, so that the evaporative cooling of the applicator nozzle can be realized efficiently. For using low temperatures via the applicator nozzle at one or more warts to treat, it is desirable to not to position and/or to attach the removable closing cap at the proximal side of the pen. The removable closing cap is preferably made of polymers and preferably produced via injection moulding in a mould. The removable closing cap is preferably made of styrene acryl nitrile.

Assuming the applicator having a pen shape, the diameter over the length of the pen may be substantially round. Preferably, the device comprises a grip part. Such grip part may e.g. comprise a triangular cross-section, especially having rounded angles. Hence, in yet an even more preferred embodiment, the applicator comprises different cross-sections, gradually changing from round to a grip part having a triangular cross-section (and optionally turning to a substantially round cross-section again). The applicator may include a closure. When defining the shape of the applicator, such closure may be included.

At least the housing of the device according to the present invention is made of synthetic material reinforced with glass fibres. A synthetic material reinforced with glass fibres is a strong material with a light weight that is cheaper than the high-quality lightweight materials such as aluminium and carbon fibre. This makes a synthetic material reinforced with glass fibres extremely suitable as a material for the cartridge housing and/or at least one housing of the device, since these housings can, for safety measures and for guaranteeing an efficient use of the wart pen, resist the high pressure levels cause by the coolant under increased pressure. An appropriate example of a synthetic material reinforced with glass fibres is polyoxymethylene reinforced with glass fibres.

According to an embodiment of the first aspect of the invention, the housing of the device has a maximum compressive force of 1850 N to 6400 N, measured according to ASTM D695-10. Similar values of maximum compressive force for housings of the wart pens are important for resisting the high pressure levels exercised by a coolant under increased pressure that is present in the wart pen.

In a second aspect, the present invention provides an actuator assembly suitable for cryogenic device for controlling an outflow of a cryogenic fluid, wherein said actuator assembly comprises at least one spring leaf and a needle, whereby said spring leaf is bearing against a ball of a ball valve. In a preferred embodiment, the actuator assembly of the invention comprises sealing o-rings. Preferably, a support face for said sealing o-rings is flat. The actuator mechanism of the invention can be sealed without almost any audible sound, thus it is suitable for vide variety of actuator pen and nozzle designs. The absence of audible signal when sealing the actuator assembly to a pen leads to easier use and no confusion when a user seals the actuator assembly to a pen and when the mechanism is actuated by piercing of a cryogenic cartridge with a needle. This leads to a safer use of cryogenic devices comprising said actuator assembly and more reliable application of the cryogenic fluid. The design of the actuator assembly comprising at least one spring leaf and a needle, whereby said spring leaf is bearing against a ball of a ball valve and whereby the sealing is facilitated by sealing o-rings is relatively simple compared to other known mechanisms, the cost of production is low and said assembly is compatible and suitable for various cryogenic fluids.

It should be understood by a skilled person that the actuator assembly of the invention is particularly suitable for cryogenic pens and cryogenic fluid applicators comprising a cartridge, but can be used for any type of cryogenic surgery probe, or the like.

Actuator Mechanism

In another aspect, the present invention relates to a cryogenic applicator pen comprising an actuator assembly for controlling an outflow of a cryogenic fluid, wherein said actuator assembly comprises at comprises at least one spring leaf, wherein said spring leaf on one side bears against a ball of a ball valve and on an opposite side bears against a positioning casing bearing a needle for piercing a cryogenic fluid cartridge.

In a preferred embodiment, the said needle used for piercing a cryogenic fluid cartridge is secured within a foot of a spring leaf positioning casing.

In a preferred embodiment, the actuator assembly comprises at least two spring leaves. In a further preferred embodiment, the actuator assembly comprises two spring leaves.

In a further preferred embodiment, at least one of said spring leaves is made of thermoplastic material. In a particularly preferred embodiments, said polymer material, preferably resilient plastic polymer material, most preferably polyoxymethylene.

In a further preferred embodiment, said actuator assembly is made of thermoplastic material. In a further preferred embodiment, said thermoplastic material is a polymer material. In a preferred embodiment, the applicator nozzle and/or the actuator stem are comprised of a polymer material. The integrated actuator assembly design with spring leaf made of polymer material is easier to produce and less costly than known actuator mechanisms comprising metal parts and known in the prior art. Moreover, the parts of such actuator mechanism give more pronounced audible and haptic feedback signals that device is ready to be used than metal spring leaves known in the prior art. Thus, the actuator assembly is easier to use and more reliable than similar devices in the prior art.

It should be understood by a skilled person that said polymer materials for the said spring leaves, applicator nozzle and/or the actuator stem are, independently, selected from the group consisting of chlorinated polyvinyl chloride (CPVC), ethylene chlorotrifluoroethylene (ECTFE), (enhanced) polytetrafluoroethylene, (enhanced PTFE), high-density poly ethylene (HDPE), polyether ether ketone (PEEK), polypropylene (PP), polysulfone (PSU), polyphenylene sulfide (PPS), polyvinyl chloride (especially type 1 (PVC, Type 1) or type 2 (PVC, Type 2)), polyvinylidene fluoride (PVDF), polytetrafluoroethylene (PTFE), Polyamide-imide (PAI), ultra-high molecular weight polyethylene (UHMW) and also coated. Yet in a further embodiment, good materials for the said spring leaf, applicator nozzle and/or the actuator stem may independently be selected from the group consisting of high-density poly ethylene (HDPE), low-density poly ethylene (LDPE), polyamide (PA), polycarbonate (PC), polyethylene terephthalate (PET) (including e.g. polyethylene terephthalate glycol PETG), polymethylpentene (PMP), polyoxymethylene (POM), polypropylene (PP), polystyrene (PS), polysulfone (PSU), polyvinyl chloride (especially rigid (PVC HART) and flexible (PVC WEICH), styrene acrylonitrile (SAN), ethylene chlorotrifluoroethylene (ECTFE), ethylene chlorotrifluoroethylene (ETFE), fluorinated ethylene propylene (FEP), polytetrafluoroethylene (PTFE), polyvinylidene fluoride (PVDF), ethylene propylene diene rubber (EPDM), fluorocarbon rubber (FPM), and acrylonitrile (nitrile) butadiene rubber (NBR), without departing from the scope of the invention.

The advantage of said mechanism is easier and cleaner application of the cryogenic fluid. Furthermore this preserves the pressurized cryogenic fluid in the cartridge while the device is not in use.

The cryogenic applicator pen according to the present invention is appropriate for the treatment of dermatological disorders, such as warts, by means of low temperatures that can be reached at the applicator surface of the pen. These low temperatures are generated when a cryogenic fluid coolant, with a low boiling point, evaporates quickly at the applicator at environmental temperature or at body temperature of a human body. The heat required for the evaporation of the cryogenic fluid coolant is withdrawn from the applicator nozzle, so that the applicator surface cools down to low temperatures. In other words, the applicator surface is cooled down to low temperatures by means of evaporative cooling. The use of an applicator surface cooled down to a low temperature at the dermatological area to treat causes the destruction of present dermatological disorders by killing the cells. The obtained evaporative cooling achieves temperatures that are sufficiently low for the treatment of dermatological disorders, without causing hypothermia and/or without undesired interaction of the low temperatures with areas that do not require treatment, such as, for example, healthy skin tissue surrounding a dermatological disorder. Several dermatological disorders such as for example warts, hyperpigmentation and fibroma, can be treated by using the obtained evaporative cooling.

It should be understood by a skilled person that any suitable cryogenic fluid can be used as a coolant in a cryogenic actuator pen and the actuator assembly, without departing from the scope of the invention. Some of the non-limiting examples of said cryogenic fluid are dimethyl ether, n-butane, isobutene, propane, nitrogen, dinitrogen oxide and/or halogenated hydrocarbons such as, for example, tetrafluoromethane, trifluoromethane and 1,1,1,2-tetrafluoroethane, and the like. A skilled worker will understand that because of the relatively high internal pressure that is present in the holder, chemical agents can be present in the form of a liquid or a gas/liquid mixture. For cryogenic fluid coolants in the form of a liquid, the term liquid coolant is used. For coolants in the form of a gas, the term gaseous coolant is used. Moreover, a skilled worker will understand that a coolant can consist of several different chemical agents in order to decrease the internal pressure of the holder necessary for achieving a desired boiling point.

In a preferred embodiment, said actuator assembly comprises at least two spring leaves, whereby at least one spring leave comprises a longitudinal protuberance for positioning a ball in said ball valve. In a further preferred embodiment, actuator assembly comprises at least two spring leaves, whereby at least two spring leave comprises a longitudinal protuberance for positioning a ball in said ball valve. In a preferred embodiment, said actuator assembly comprises at least one ring hook on a connection means for connecting the actuator assembly to at least two ring hook segments of housing comprising a cryogenic fluid cartridge.

The integrated actuator assembly of the present invention comprises two positions. The first position will be called "closed", the second will be called "open". When the integrated actuator assembly is in the closed position, the actuating stem closes off the applicator nozzle. When the integrated actuator assembly is in the open position, the actuating stem allows fluid communication between the cryogenic fluid cartridge and the applicator nozzle along the actuator stem. If the actuating stem is moved from the closed position to the open position while the cryogenic fluid cartridge is intact, a needle will pierce said cryogenic fluid cartridge. In a preferred embodiment, said needle is a flat needle. In another preferred embodiment, said needle is a beveled needle.

This will open the cryogenic fluid cartridge, allowing fluid communication between the cryogenic fluid cartridge and the applicator nozzle. Additionally, the actuator assembly comprises two positions for the actuating stem. The "actuator assembly" comprises the "actuating stem" but can comprise additional elements.

In a preferred embodiment, said cryogenic fluid is carbon dioxide. When the actuating mechanism is in the open position, the actuating stem allows fluid communication between the carbon dioxide cartridge and the applicator nozzle along the actuator stem. If the actuating stem is moved from the closed position to the open position while the carbon dioxide cartridge is intact, a needle will pierce said carbon dioxide cartridge. This will open the carbon dioxide cartridge, allowing fluid communication between the carbon dioxide cartridge and the applicator nozzle. Additionally, the actuator mechanism comprises two positions for the actuating stem. The "actuator mechanism" comprises the "actuating stem" but can comprise additional elements. In a preferred embodiment of the invention, the actuator stem is biased towards the first position wherein the actuator stem closes off the opening of the applicator nozzle. The advantage is that moving the actuator stem to the open, unbiased position requires an action. This ensures that carbon dioxide is only released when desired. It also helps to avoid leaks and spills. Also, a bias towards the first, closed position reduces the chances for human error when closing the carbon dioxide cartridge.

In a further embodiment, the actuator mechanism comprises a spring for biasing said actuator stem in the first position. A spring is a cheap and reliable tool. Preferably, said spring is a leaf spring. They are well known, reliable and fit for use in medical devices.

The advantage of said mechanism is easier and cleaner application of the carbon dioxide. Furthermore this preserves the pressurized carbon dioxide in the cartridge while the device is not in use.

The advantage of said mechanism is easier and cleaner application of the cryogenic fluid coolant. Furthermore this preserves the pressurized cryogenic fluid in the cartridge while the device is not in use.

In a preferred embodiment of the invention, the actuator stem is biased towards the first position wherein the actuator stem closes off the opening of the applicator nozzle. The advantage is that moving the actuator stem to the open, unbiased position requires an action. This ensures that the cryogenic fluid is only released when desired. It also helps to avoid leaks and spills. Also, a bias towards the first, closed position reduces the chances for human error when closing the cryogenic fluid cartridge.

In a preferred embodiment, the actuator assembly comprises a spring for biasing said actuator stem in the first position. A spring is a cheap and reliable tool. Preferably, said spring is a leaf spring. They are well known, reliable and fit for use in medical devices.

In a further preferred embodiment, the cryogenic applicator pen comprises at least one spring leaf and said needle in a positioning casing of the said actuator assembly.

In a preferred embodiment, the present invention provides a cryogenic applicator pen according to the first aspect of the invention, wherein said actuator assembly for controlling an outflow of the cryogenic fluid from said pressurized cryogenic fluid cartridge to said applicator nozzle comprises at least one spring leaf, wherein said spring leaf on one side bears against a ball of a ball valve and on an opposite side bears against a positioning casing bearing a needle for piercing a cryogenic fluid cartridge. The ball valve preferably contains a ball that is resiliently biased against a ball seat. The ball seat has a tubular shape whereby the longitudinal axis of said tube corresponds to a radial axis of said ball. This means that the longitudinal axis of said tube runs through the center of said ball. Importantly, the ball seat tube has one concave contact surface faced towards said ball. Said ball corresponds in size and shape to said ball seat. Accordingly, the ball valve is configured to close off the part of the coolant passage way. The resilient bearing of the ball means that the ball rests on a spring in the direction of the applicator nozzle of the device, thus downstream of the cryogenic fluid cartridge. The axis of the spring is preferably oriented according to the length axis of the device and of the cryogenic fluid cartridge. The spring supports the position of the ball. At presence of cryogenic fluid at the valve, an internal pressure resulting from the coolant contributes to the connection of the ball against the ball seat. When an external, actuating pressure is exercised on the proximal part of the device, oriented against the force of the spring and the internal pressure, the spring will contribute to maintaining the position of the ball with respect to the axis of the spring, thereby rendering the ball valve in the open position. The ball and spring preferably consist of a material that is resistant to corrosion by contact with the coolant and that can resist to high internal pressure levels exercised by the coolant as well as the low temperatures of the coolant. The ball and spring can for example be made of metal, preferably stainless steel.

In a preferred embodiment, the present invention provides a device according to the first aspect of the invention, wherein the concave contact surface of the ball seat is provided with one or more flow restriction channels for conducting the cryogenic fluid and for restricting its flow. A flow restriction channel is preferably to be understood as a recession in said concave contact surface. The recession can have an angular or a circular cross-section. Preferably, said flow restriction channel runs straight from a point on the outer circumference of said tube to a point on the inner circumference of said tube. This means that said flow restriction channel is within a plane running through the longitudinal axis of said tube. Surprisingly, the guidance of cryogenic fluid through the flow restriction channels is very important for the formation of a cryogenic fluid tablet with good mechanical properties. The inventors have found that preferably two or more flow restriction channels are provided within said concave contact surface. More preferably, said two or more flow restriction channels are provided symmetrically around the internal hollow space of the ball seat tube. This means that in case of two flow restriction channels these channels are provided under an angle of 180° relative to each other; in case of three flow restriction channels these channels are provided under an angle of 120° relative to each other; in case of four flow restriction channels these channels are provided under an angle of 90° relative to each other; in case of five flow restriction channels these channels are provided under an angle of 72° relative to each other; in case of six flow restriction channels these channels are provided under an angle of 60° relative to each other; etc. More preferably, said concave contact surface is provided with two, three, four, five or six flow restriction channels, and more preferably with three or four flow restriction channels.

In a further embodiment, the actuator mechanism comprises a spring for biasing said actuator stem in the first position. A spring is a cheap and reliable tool. Preferably, said spring is a leaf spring. They are well known, reliable and fit for use in medical devices.

In a further preferred embodiment, the cryogenic applicator pen comprises the actuator assembly which is activated by one direction twist move of a cryogenic applicator pen. In a further preferred embodiment, said activation of the cryogenic applicator pen is followed by a haptic feedback signal to an operator. The ring hook system of a connection means for connecting the actuator assembly to at least two ring hook segments of housing comprising a cryogenic fluid cartridge facilitates silent arming step, with no "click" sound. In a preferred embodiment, the actuator assembly of the invention comprises the sealing mechanism comprising sealing o-rings. Preferably, a support face for said sealing o-rings is flat. The actuator mechanism of the invention can be sealed without almost any audible sound. As there are no radial hooks to overcome, said arming results in smooth turning with the noticeable haptic feedback signal only when the needle pierces the cryogenic fluid cartridge. The present system gives the clear guidance, i.e. a haptic signal to a user when the applicator pen is ready for use, while arming step is silent. Moreover, the present ring hook connection system requires the reduced arming force in comparison to previously known similar cryogenic devices. The pen is thus easier to operate with and creates no confusion is which direction should be twisted, as the only one direction is possible. These features all lead to easier and safer application of said applicator pen onto the skin to a subject in need. Moreover, such assembly reduces the risk of errors during assembly of the cryogenic applicator pen and it is cheaper to known assembly mechanisms.

In a preferred embodiment of the invention, the actuator stem is biased towards the first position wherein the actuator stem closes off the opening of the applicator nozzle. The advantage is that moving the actuator stem to the open, unbiased position requires an action. This ensures that carbon dioxide is only released when desired. It also helps to avoid leaks and spills. Also, a bias towards the first, closed position reduces the chances for human error when closing the carbon dioxide cartridge.

In a further embodiment, the actuator mechanism comprises a spring for biasing said actuator stem in the first position. A spring is a cheap and reliable tool. Preferably, said spring is a leaf spring. They are well known, reliable and fit for use in medical devices.

In a preferred embodiment, the present invention provides a device according to the first aspect of the invention, wherein said actuator mechanism for controlling an outflow of carbon dioxide from said pressurized carbon dioxide cartridge to said applicator nozzle comprises a ball valve. The ball valve preferably contains a ball that is resiliently biased against a ball seat. The ball seat has a tubular shape whereby the longitudinal axis of said tube corresponds to a radial axis of said ball. This means that the longitudinal axis of said tube runs through the centre of said ball. Importantly, the ball seat tube has one concave contact surface faced towards said ball. Said ball corresponds in size and shape to said ball seat. Accordingly, the ball valve is configured to close off the part of the coolant passage way. The resilient bearing of the ball means that the ball rests on a spring in the direction of the applicator nozzle of the device, thus downstream of the carbon dioxide cartridge. The axis of the spring is preferably oriented according to the length axis of the device and of the carbon dioxide cartridge. The spring supports the position of the ball. At presence of carbon dioxide gas at the valve, an internal pressure resulting from the coolant contributes to the connection of the ball against the ball seat. When an external, actuating pressure is exercised on the proximal part of the device, oriented against the force of the spring and the internal pressure, the spring will contribute to maintaining the position of the ball with respect to the axis of the spring, thereby rendering the ball valve in the open position. The ball and spring preferably consist of a material that is resistant to corrosion by contact with the coolant and that can resist to high internal pressure levels exercised by the coolant as well as the low temperatures of the coolant. The ball and spring can for example be made of metal, preferably stainless steel.

In a preferred embodiment, the present invention provides a device according to the first aspect of the invention, wherein the concave contact surface of the ball seat is provided with one or more flow restriction channels for conducting carbon dioxide and for restricting its flow. A flow restriction channel is preferably to be understood as a recession in said concave contact surface. The recession can have an angular or a circular cross-section. Preferably, said flow restriction channel runs straight from a point on the outer circumference of said tube to a point on the inner circumference of said tube. This means that said flow restriction channel is within a plane running through the longitudinal axis of said tube. Surprisingly, the guidance of carbon dioxide through the flow restriction channels is very important for the formation of a carbon dioxide tablet with good mechanical properties. The inventors have found that preferably two or more flow restriction channels are provided within said concave contact surface. More preferably, said two or more flow restriction channels are provided symmetrically around the internal hollow space of the ball seat tube. This means that in case of two flow restriction channels these channels are provided under an angle of 180° relative to each other; in case of three flow restriction channels these channels are provided under an angle of 120° relative to each other; in case of four flow restriction channels these channels are provided under an angle of 90° relative to each other; in case of five flow restriction channels these channels are provided under an angle of 72° relative to each other; in case of six flow restriction channels these channels are provided under an angle of 60° relative to each other; etc. More preferably, said concave contact surface is provided with two, three, four, five or six flow restriction channels, and more preferably with three or four flow restriction channels.

Other

In a preferred embodiment, the present invention provides a device according to the first aspect of the invention, wherein said sublimation chamber has a volume of between 0.1 $cm^3$ to 5.0 $cm^3$. Preferably, said sublimation chamber has a volume of higher than 0.1 $cm^3$, higher than 0.2 $cm^3$, higher than 0.3 $cm^3$, higher than 0.5 $cm^3$, higher than 0.8 $cm^3$, or even higher than 1.0 $cm^3$. This allows for the formation of a tablet with a sufficiently high volume and thus a sufficiently high cooling ability. Preferably, said sublimation chamber has a volume of smaller than 5.0 $cm^3$, smaller than 4.0 $cm^3$, smaller than 3.0 $cm^3$, smaller than 2.5 $cm^3$, or even smaller than 2.0 $cm^3$. A carbon dioxide tablet with a volume which is too large may cause damage to the skin tissue when the cooling is applied too long.

In a preferred embodiment, the applicator comprises an applicator nozzle comprising a surface having e.g. a surface or contact area in the range of 0.01-4.0 $cm^2$, such as 0.1-2.5 $cm^2$.

Assuming the applicator having a pen shape, the diameter over the length of the pen may be substantially round. Preferably, the device comprises a grip part. Such grip part may e.g. comprise a triangular cross-section, especially having rounded angles. Hence, in yet an even more preferred embodiment, the applicator comprises different cross-sections, gradually changing from round to a grip part having a triangular cross-section (and optionally turning to a substantially round cross-section again). The applicator may include a closure. When defining the shape of the applicator, such closure may be included.

At least the housing of the device according to the present invention is made of synthetic material reinforced with glass fibres. A synthetic material reinforced with glass fibres is a strong material with a light weight that is cheaper than the high-quality lightweight materials such as aluminium and carbon fibre. This makes a synthetic material reinforced with glass fibres extremely suitable as a material for the cartridge housing and/or at least one housing of the device, since these housings can, for safety measures and for guaranteeing an efficient use of the wart pen, resist the high pressure levels cause by the coolant under increased pressure. An appropriate example of a synthetic material reinforced with glass fibres is polyoxymethylene reinforced with glass fibres.

According to an embodiment of the first aspect of the invention, the housing of the device has a maximum compressive force of 1850 N to 6400 N, measured according to ASTM D695-10. Similar values of maximum compressive force for housings of the wart pens are important for resisting the high pressure levels exercised by a coolant under increased pressure that is present in the wart pen.

The applicator nozzle, the actuator stem and/or said spring are preferably comprised of a polymer material. Good polymer materials for the applicator nozzle, the actuator stem and/or said spring may be, independently, selected from the group consisting of chlorinated polyvinyl chloride (CPVC), ethylene chlorotrifluoroethylene (ECTFE), (enhanced) polytetrafluoroethylene, (enhanced PTFE), high-density poly ethylene (HDPE), polyether ether ketone (PEEK), polypropylene (PP), polysulfone (PSU), polyphenylene sulfide (PPS), polyvinyl chloride (especially type 1 (PVC, Type 1) or type 2 (PVC, Type 2)), polyvinylidene fluoride (PVDF), polytetrafluoroethylene (PTFE), Polyamide-imide (PAI), ultra-high molecular weight polyethylene (UHMW) and also coated. Yet in a further embodiment, good materials for the applicator nozzle, the actuator stem and/or said spring may independently be selected from the group consisting of high-density poly ethylene (HDPE), low-density poly ethylene (LDPE), polyamide (PA), polycarbonate (PC), polyethylene terephthalate (PET) (including e.g. polyethylene terephthalate glycol PETG), polymethylpentene (PMP), polyoxymethylene (POM), polypropylene (PP), polystyrene (PS), polysulfone (PSU), polyvinyl chloride (especially rigid (PVC HART) and flexible (PVC WEICH), styrene acrylonitrile (SAN), ethylene chlorotrifluoroethylene (ECTFE), ethylene chlorotrifluoroethylene (ETFE), fluorinated ethylene propylene (FEP), polytetrafluoroethylene (PTFE), polyvinylidene fluoride (PVDF), ethylene propylene diene rubber (EPDM), fluorocarbon rubber (FPM), and acrylonitrile (nitrile) butadiene rubber (NBR).

In a preferred embodiment, the medicament device further comprises a removable closing cap for protecting the applicator nozzle. The cap can be placed over the nozzle preventing damage to the nozzle or the accidental actuation of the actuator mechanism.

Kit for Assembling a Device for the Topical Cryotherapy

In a further aspect, the invention provides a kit for assembling a device for the topical cryotherapy of dermatological disorders, such as warts, in a subject in need thereof, the kit comprising:

- a housing for holding a cryogenic fluid cartridge;
- a cryogenic fluid cartridge;
- an applicator nozzle comprising (i) an internal channel for guiding the outflow of cryogenic fluid from said cryogenic fluid cartridge, and (ii) an applicator surface onto which cryogenic fluid ice may be formed;
- an actuator assembly suitable for cryogenic device, wherein said actuator assembly comprises at least one spring leaf and a needle, whereby said spring leaf is bearing against a ball of a ball valve for controlling an outflow of cryogenic fluid from said cryogenic fluid cartridge to said applicator nozzle, which actuator assembly is movable between a first, closed position and between a second, open position.

In a preferred embodiment, said kit further comprises a removable closing cap, detachably provided across from said applicator nozzle, said closing cap comprising a cup which, in an arranged position, faces towards said applicator nozzle, thereby forming a chamber between said cup of said closing cap and said applicator nozzle; whereby said cup, in said arranged position, obstructs the outflow of the cryogenic fluid from said applicator nozzle.

Preferably, said kit is configured for assembling a cryogenic applicator pen according to the first aspect of the invention.

In a preferred embodiment, the present invention provides a kit for assembling a device for the topical cryotherapy of dermatological disorders, such as warts, in a subject in need thereof, the kit comprising:

- a housing for holding a pressurized carbon dioxide cartridge;
- an applicator nozzle comprising (i) an internal channel for guiding the outflow of carbon dioxide from said pressurized carbon dioxide cartridge, and (ii) an applicator surface onto which carbon dioxide ice may be formed and compacted;
- an actuator mechanism for controlling an outflow of carbon dioxide from said pressurized carbon dioxide cartridge to said applicator nozzle, which actuator mechanism is movable between a first, closed position and between a second, open position.

In a preferred embodiment, said kit further comprises a closing cap, detachably provided across from said applicator nozzle, said closing cap comprising a cup which, in an arranged position, faces towards said applicator nozzle, thereby forming a sublimation chamber between said cup of said closing cap and said applicator nozzle; whereby said cup, in said arranged position, obstructs the outflow of carbon dioxide gas from said applicator nozzle, thereby forming solid carbon dioxide crystals within said sublimation chamber.

Preferably, said kit is configured for assembling a device according to the first aspect of the invention.

Method for the administration of the cryogenic applicator pen or the cryogenic device comprising the actuator assembly of the invention In a further aspect, the present invention provides a method for the administration of the cryogenic applicator pen or the cryogenic device comprising the actuator assembly of the invention, which method comprises:

- providing the pen and/or cryogenic device for the treatment of dermatological disorders;
- arming of said pen and/or cryogenic device with a cryogenic fluid cartridge onto the said actuator assembly of an applicator of said pen and/or device using a ring hook connecting means to close an assembly;
- piercing of said cryogenic fluid cartridge by a needle secured onto the foot of a positioning casing of the actuator assembly;
- flowing the cryogenic fluid under increased pressure from the cryogenic fluid cartridge to the valve body;
- exercising an external pressure onto the applicator end of the pen, which external pressure is exercised in opposite direction to the pressure exercised by the cryogenic fluid;
- flowing the cryogenic fluid past the valve body to the applicator;
- realizing the evaporative cooling at the applicator;
- removing the closing cap from the pen and/or cryogenic device.

The invention is further described by the following non-limiting examples which further illustrate the invention, and are not intended to, nor should they be interpreted to, limit the scope of the invention.

EXAMPLE

A preferred embodiment of the present invention is presented below. It is however clear that other embodiments can easily be contemplated within the scope of the invention. The presentation below should thus not be construed restrictive, but it should be realized that the skilled person will easily apply modifications to the presented example without reappraisal of the appended claims.

Example 1

Figure 2A:
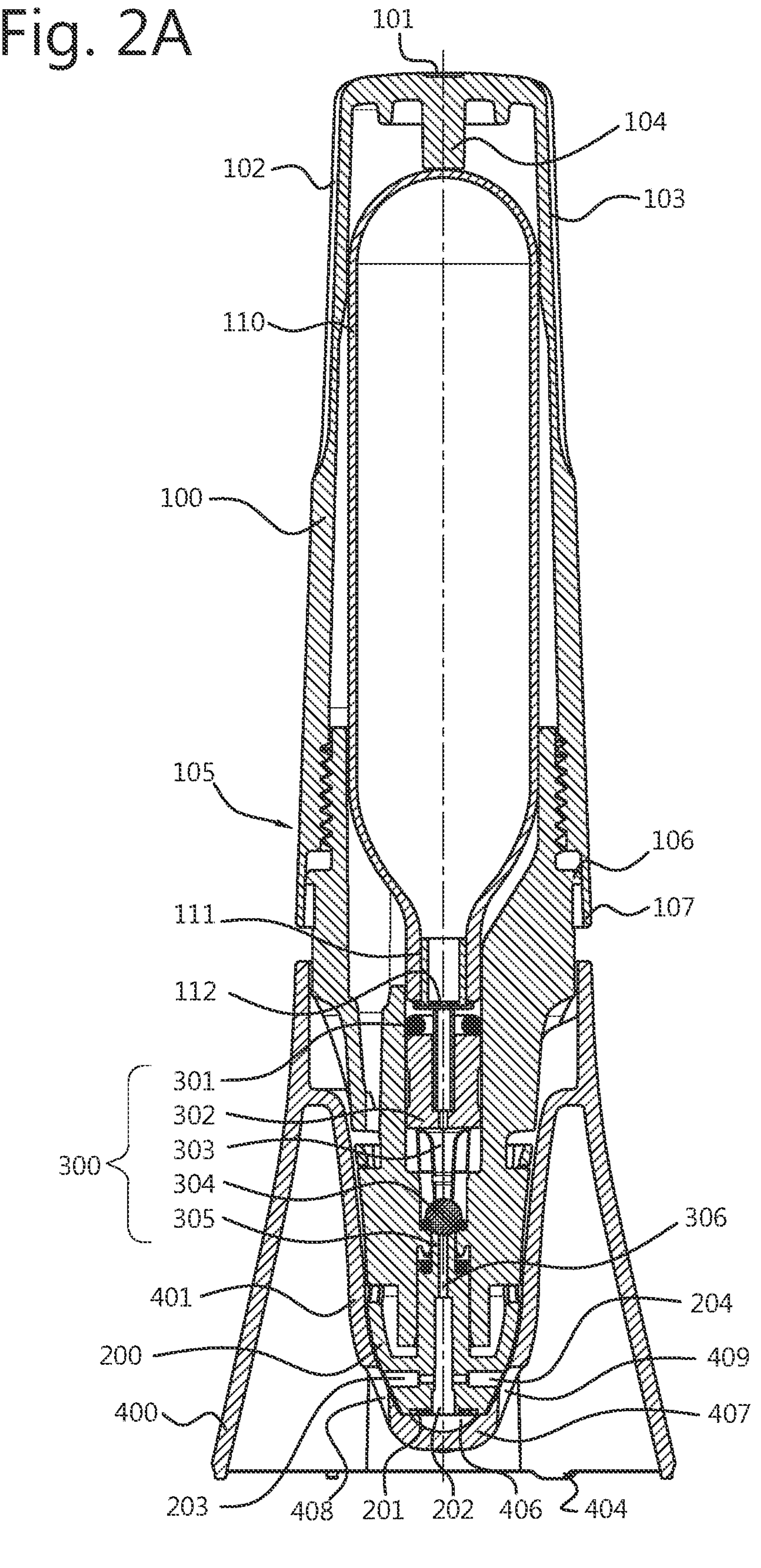
FIG. 2A shows a first cross-section in the longitudinal direction of the device of a possible embodiment of a cryogenic applicator pen of the invention, wherein the actuator assembly valve is in the open position.
Figure 2B:
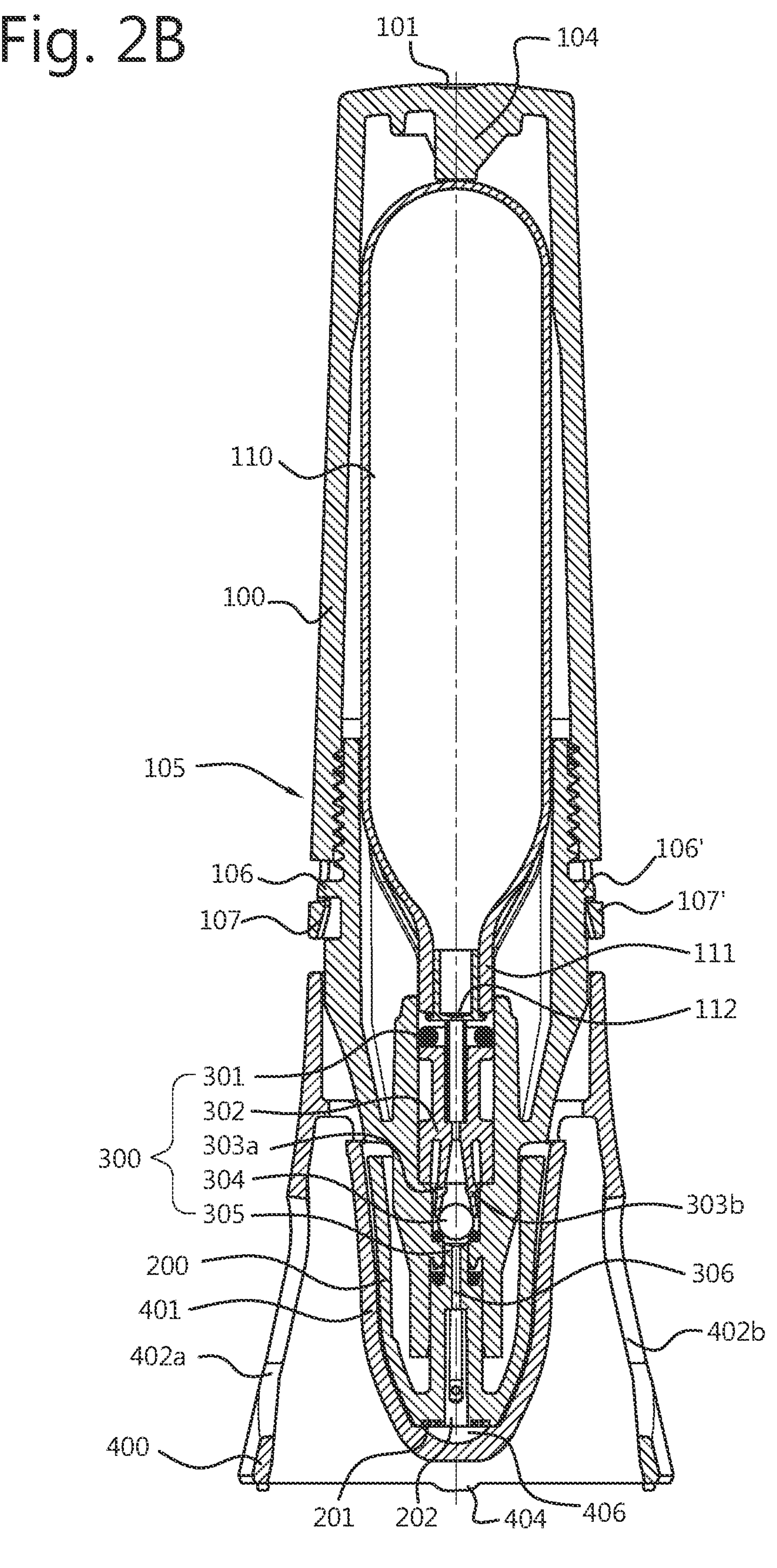
FIG. 2B shows a second cross-section in the longitudinal direction of the device and perpendicular to the first cross-section shown in FIG. 2A wherein the actuator assembly valve is in the closed position.
Figure 3A:
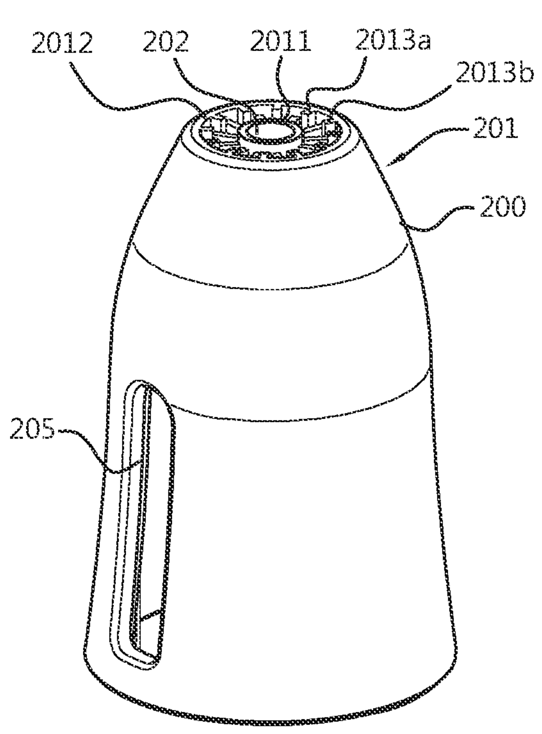
FIG. 3A shows schematically a perspective view of the applicator nozzle 200.
Figure 3B:
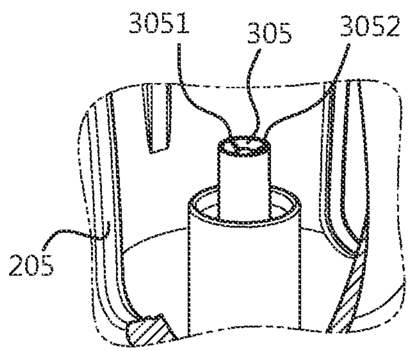
FIG. 3B shows in perspective the ball seat 305 onto which the ball 304 of the ball valve mechanism is resiliently provided.
Figure 3C:
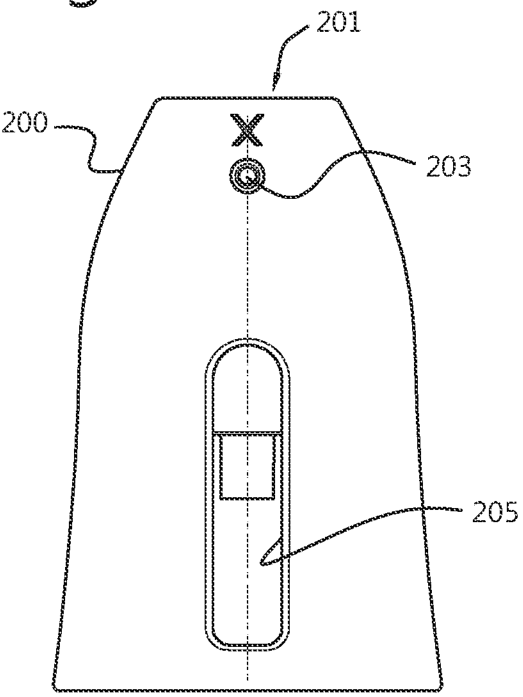
FIG. 3C shows a schematic side view of the applicator nozzle 200 of FIG. 3A.
Figures 3D, 3E:
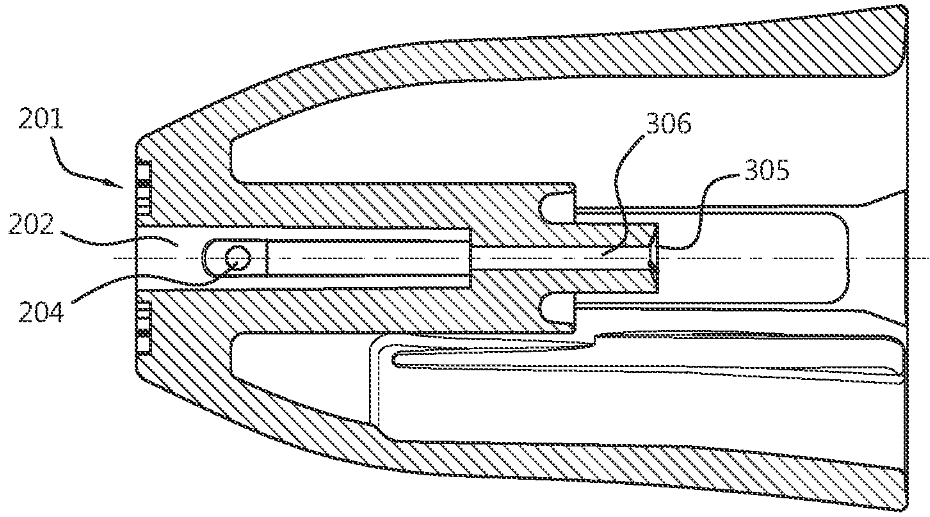
FIG. 3D shows schematically a cross-section of the applicator nozzle 200.
FIG. 3E shows a cross-section of the applicator nozzle 200 whereby the cross-section is taken in the longitudinal direction of the device, perpendicular to the cross-section of FIG. 3D.

FIG. 1 shows schematically a perspective view of the device for the topical cryotherapy of dermatological disorders, such as warts, in a subject in need thereof. A first cross-section in the longitudinal direction of the device is shown in FIG. 2A. A second cross-section in the longitudinal direction of the device and perpendicular to the first cross-section shown in FIG. 2A, is shown in FIG. 2B.

The device comprises a housing 100 for holding cryogenic fluid cartridge 110, whereby said cryogenic fluid is preferably a pressurized carbon dioxide and a closing cap 400, detachably provided at the applicator end of the housing 100. The housing 100 is provided with an anti-roll design feature 1000. The housing 100 is at the distal end provided with two grip recesses 102, 103. Also at its distal end, the housing 100 is provided with a centring protrusion 101, 104.

The actuator mechanism for controlling an outflow of a cryogenic fluid, preferably carbon dioxide 300 is provided on top of the seal 112 at the neck 111 of the carbon dioxide cartridge 110. The actuator mechanism for controlling an outflow of a cryogenic fluid 300 is fastened within the housing 100 using fastening means 105, 106, 107. Said fastening means comprise at least one ring hook on a fastening means 105*a* for connecting the integrated actuator assembly to at least two ring hook segments 108*a*', 108*aa*' of fastening system 108 of housing 100 comprising a cryogenic fluid cartridge. The fastening means 105, 106, 107, 108 ensure that the cryogenic fluid cartridge 110 is fixed between the housing 100 and the integrated actuator assembly 300 upon closing of the housing 100 and the integrated actuator assembly 300. In a preferred embodiment, the fastening means 106, 107 ensure that the carbon dioxide cartridge 110 is fixed between the housing 100 and the actuator mechanism 300 upon closing of the housing 100 and the actuator mechanism 300. This means that upon closing of the assembly 100.300, the assembly 100.300 cannot be opened again. This ensures that the operator cannot come directly into contact with the high-pressure environment of the device. The fastening means 106, 107 consist of one ring hook 106-106' comprising a ramp-up zone over which the resilient ring 107-107' is passed. The ramp-up zone allows for a unidirectional motion of the housing 100. Once the resilient ring 107-107' has passed over the ring hook 106-106', the return movement is prohibited, thereby preventing the assembly 100.300 to be disassembled. Moreover, said fastening means 105, 106, 107, 108 ensure smooth and silent closing of the assembly 100.300. Thus, closing of the assembly 100.300 produces no "click" sound which could be confused with a sound of perforation of a cryogen fluid cartridge of said cryogenic applicator pen. Thus, the application of said pen is easier and with less errors.

Upon actuation, a needle 307 for piercing a cryogenic fluid cartridge perforates the seal 112 of the cryogenic fluid cartridge 110 and the seal 112 of the cartridge 110 is broken. Accordingly, a fluid communication channel is established between the contents of the cryogenic fluid cartridge 110, preferably carbon dioxide cartridge and the internal channel 202 of the applicator nozzle 200. The fluid communication channel is interrupted by a ball valve mechanism 301, 302, 303, 304, 305. The ball valve mechanism comprises a ball 304 resiliently positioned in front of the passage 306 leading up to the internal channel 202 of the applicator nozzle 200. The needle 307 is secured within a foot 308 of a spring leaf positioning casing 302. Sealing o-rings 301 are allowing a single seal solution. The support face of said o-rings 301 is flat. A light click is noticeable when the actuator mechanism seals to a cartridge. FIGS. 2A and 2B show a leaf spring 303*a*, 303*b*, made from a resilient plastic material such as polyoxymethylene, employed for the resilient positioning of the ball 304. The closed position, the position in which the ball 304 obstructs the outflow of carbon dioxide, is depicted in FIG. 2A. The open position, the position in which carbon dioxide may freely pass by the ball 304, is depicted in FIG. 2B.

The actuation mechanism is further conceptualized that a pressure in the longitudinal direction of the device against the surrounding rim around the applicator surface 201 of the applicator nozzle 200 causes the opening of the ball valve mechanism 301, 302, 303, 304, 305. Upon de-actuation, the device returns to the biased, closed state, thereby ceasing the outflow of the cryogenic fluid. In a preferred embodiment said cryogenic fluid is carbon dioxide.

In the open, actuated position, as depicted in FIG. 2B, the cryogenic fluid, preferably carbon dioxide flows through the passage 306 into the internal channel 202 of the applicator nozzle 200. The passage 306 and the internal channel 202 are conceptualized to provide a laminar outflow of the cryogenic fluid, preferably carbon dioxide. Turbulent flow is preferably avoided within the internal channel 202, as said turbulent flow prevents controlled formation of a compact cryogenic fluid tablet of compact ice. Turbulent flow encourages formation of carbonic snow and is preferably avoided within the internal channel 202. To this end, two venting holes 203 and 204 are provided at both sides of the internal channel 202. The venting holes 203 and 204 ensure that a proper laminar flow within the internal channel 202 is enabled and that excess of the cryogenic fluid, preferably carbon dioxide can easily be evacuated, i.e. when the outflow opening of the applicator nozzle 200 gets blocked by cryogenic fluid ice.

When the cryogenic fluid, preferably carbon dioxide passes the internal channel 202, it is obstructed due to the cup wall 407. Accordingly, a turbulent cryogenic fluid flow is created within the sublimation chamber 406, and cryogenic fluid snow is formed. Due to further outflow of the cryogenic fluid, cryogenic crystals are formed and compressed within the sublimation chamber 406. Accordingly, a cryogenic fluid, preferably carbon dioxide tablet is formed onto the surface 201 of the applicator nozzle. Instead of the cup 407, the cryogenic fluid outflow can be directed onto an alternative material or can even be directed onto the skin of the subject to provide direct cooling. Excess of cryogenic fluid, preferably carbon dioxide is evacuated through the venting holes 203, 204 along the internal channel. The cup 401 is further provided with ventilation cavities 408 and 409 corresponding to the venting holes 203 and 204 to ensure a proper evacuation of excess cryogenic fluid, preferably carbon dioxide.

Although not essential for a proper working of the present inventive concept, FIGS. 1 and 2 further illustrate a specifically adapted closing cap 400 detachably provided across from the applicator nozzle 200. Said closing cap 400 comprises a cup 401, 407 which, in an arranged position, faces towards the applicator nozzle 200, thereby forming a sublimation chamber 406 between said cup 401, 407 of said closing cap 400 and said applicator nozzle 200. Said cup 401, 407, in said arranged position, obstructs the outflow of cryogenic fluid, preferably carbon dioxide gas from said applicator nozzle 200, thereby forming solid cryogenic fluid crystals, preferably carbon dioxide crystals within said sublimation chamber 406. Said cup 401, 407 is further provided with openings 408 and 409 corresponding the venting holes 203, 204 on the side of the internal channel 202 of the applicator nozzle 200. The closing cap 400 comprises an internal casing 401 for enclosing the applicator nozzle 200. The outer shield is provided with two grip recessions 403 on each side of the closing cap 400. The grip recession 403 is additionally provided with overpressure windows 402*a*, 402*b* through which excess of cryogenic snow, preferably carbonic snow can escape in case of overdosing during the formation of the cryogenic fluid tablet, preferably carbon dioxide tablet. The closing cap 400 is further provided with a base for putting the device in an upright position, whereby said base is provided with a multitude of supporting feet 404.

FIG. 3 shows in more detail the applicator nozzle 200. FIG. 3A depicts clearly the inner channel 202 having a surrounding inner wall 2011 for ensuring proper laminar flow of the cryogenic fluid, preferably carbon dioxide. The applicator surface 201 consists of a multitude of rectangular fins 2013*a*, 2013*b*, . . . on the outer surrounding rim 2012 as well as on the inner surrounding wall 2011. The fins ensure the enhancement of the contact surface of the applicator surface. This allows for a better adhesion of the formed cryogenic fluid crystals, preferably carbon dioxide crystals on the top of the applicator surface 201. The cavity 205 allows for proper evacuation of excess gases. FIG. 3C shows a schematic side view of the applicator nozzle 200 of FIG. 3A, with further indication of the venting hole 203. FIG. 3B shows in perspective the surface onto which the ball 304 of the ball valve mechanism is resiliently provided. The ball seat 305 contains one or more flow restriction channels 3051, 3052, . . . for conducting cryogenic fluid, preferably carbon dioxide and for restricting flow. FIG. 3D shows schematically a cross-section of the applicator nozzle 200. The cross-section clearly shows the inner channel 202, the cryogenic fluid, passage 306 with the ball seat 305 comprising a flow restriction channel. The applicator surface 201 comprises an inner surrounding wall 2011 and an outer surrounding rim 2012, surrounding the rectangular fins 2013 positioned in the longitudinal direction. The cross-section further shows venting holes 203, 204 across from each other on both sides of the inner channel 202. FIG. 3E shows a cross-section of the applicator nozzle 200 whereby the cross-section is taken in the longitudinal direction of the device, perpendicular to the cross-section of FIG. 3D.

Figure 4A:
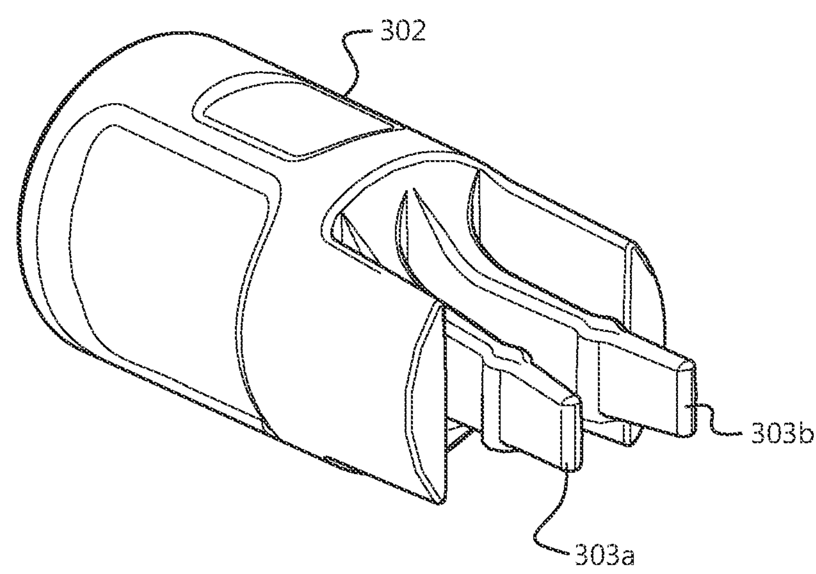
FIG. 4A shows schematically in perspective view in further detail the thermoplastic spring leaves 303*a*.303*b* comprised within a positioning casing 302.
Figure 4B:
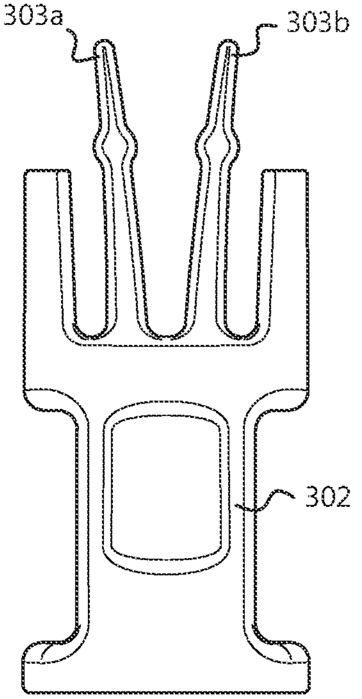
FIG. 4B shows a schematic side view of the same spring leaves 303*a*.303*b* bearing against a ball 304 of a ball valve on one side and on the other side bearing against a positioning casing 302 bearing a needle 307 for piercing a cryogenic fluid cartridge, whereby said needle 307 is secured within a foot 308 of a spring leaf positioning casing 308.
Figure 4C:
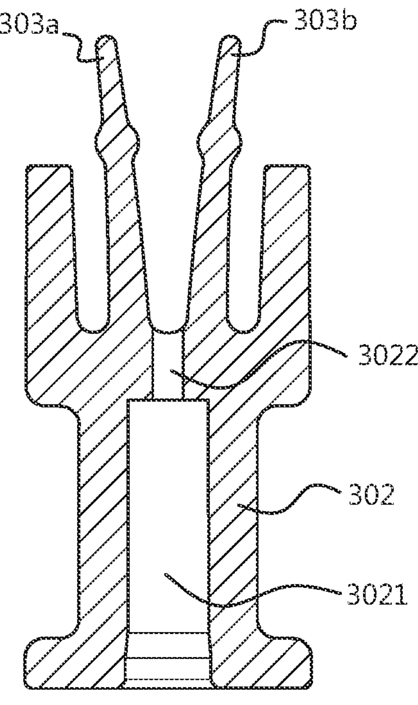
FIG. 4C shows a schematic cross-section view of the same spring leaves 303*a*.303*b*, whereby the internal passage way 3021-3022 for leading carbon dioxide outflow becomes visible.

FIG. 4A shows schematically in perspective view in further detail the thermoplastic spring leaves 303*a*.303*b* comprised within a positioning casing 302. A longitudinal protuberances 309*a* and 309*b* are comprised within the spring leaves 303*a*.303*b*, said protuberances enabling the positioning of a ball in said ball valve. FIG. 4B shows a schematic side view of the same spring leaves 303*a*.303*b*. FIG. 4C shows a schematic cross-section view of the same spring leaves 303*a*.303*b*, whereby the internal passage way 3021-3022 for leading cryogenic fluid outflow, preferably carbon dioxide outflow becomes visible.

Figure 5A:
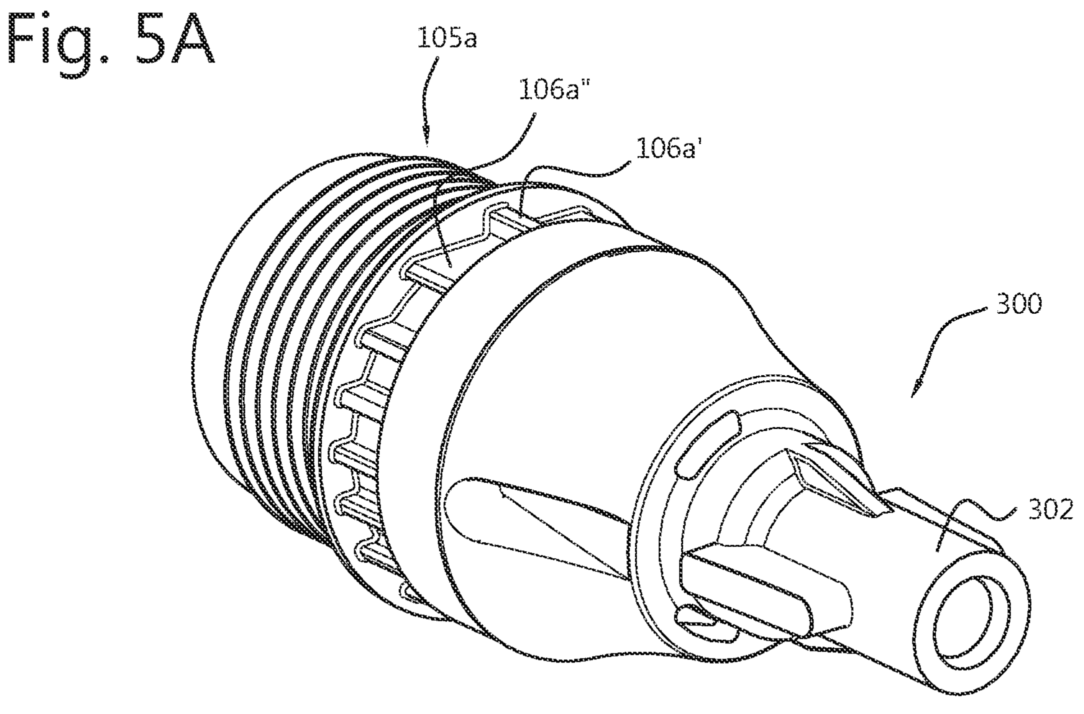
FIG. 5A and FIG. 5B show schematically a perspective view of the actuator mechanism 300 including connection means 105*a* for connecting the housing 100 comprising the carbon dioxide cartridge 110.
Figure 5B:
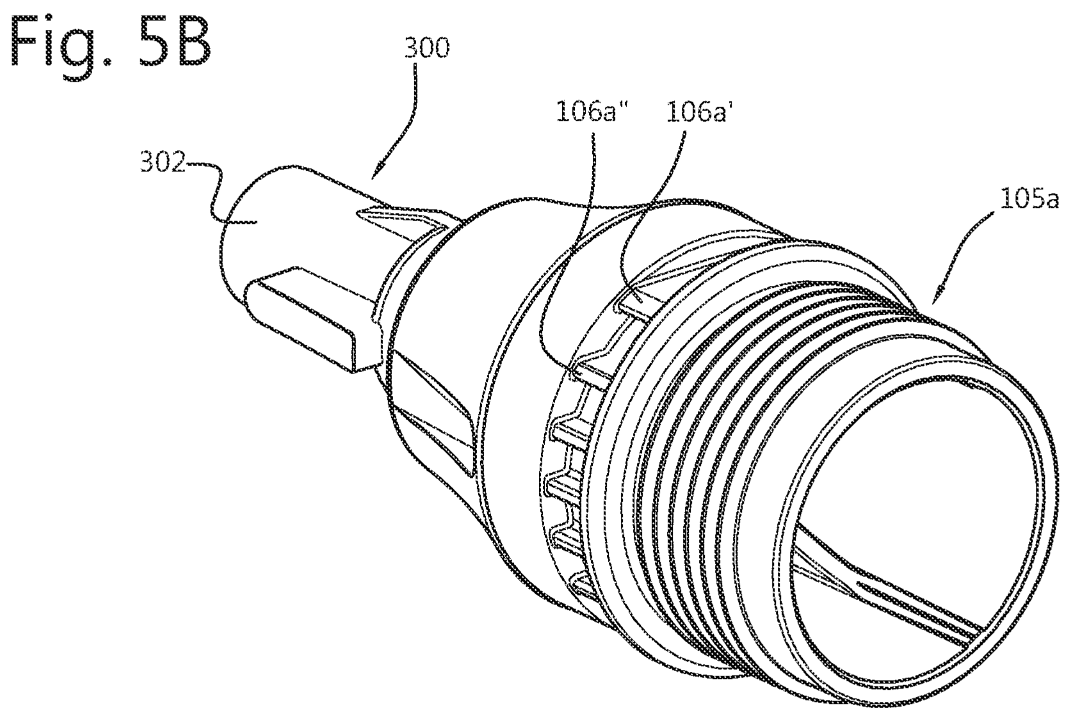
Figure 5C:
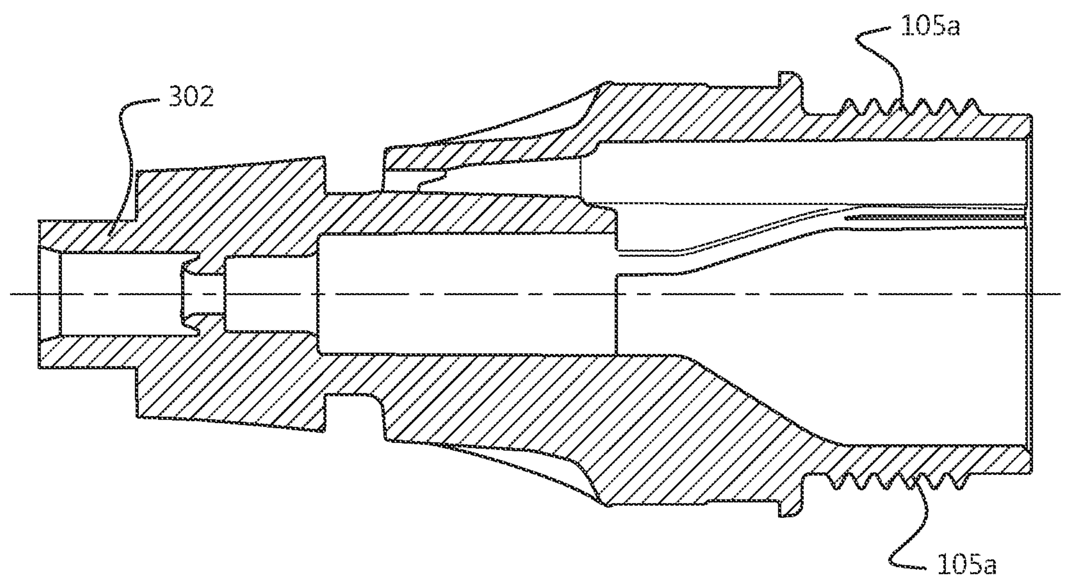
FIG. 5C shows a schematic cross-sectional view of the same actuator mechanism 300 as FIG. 5A.
Figure 5D:
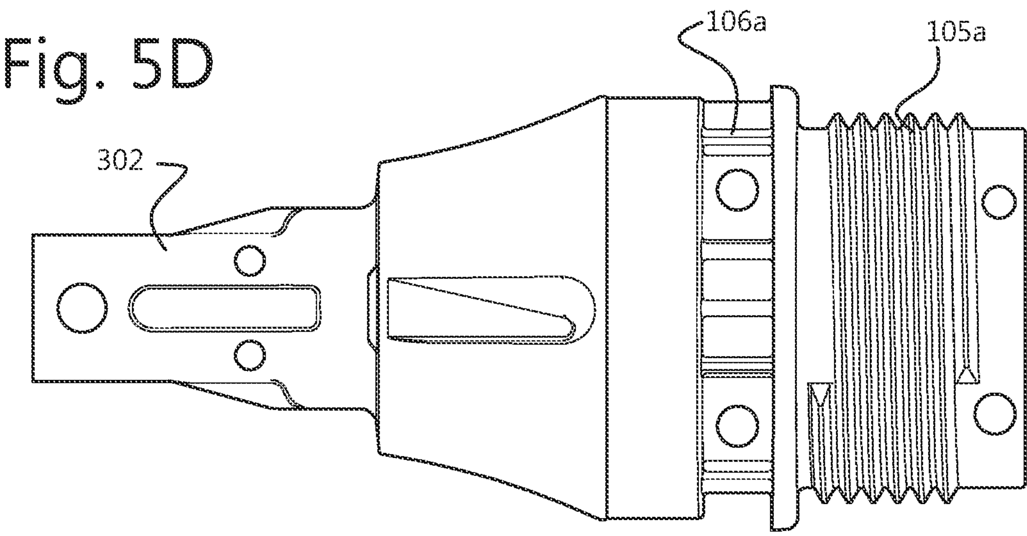
FIG. 5D shows a schematic side view of the same actuator mechanism 300 as FIG. 5A.

FIG. 5A and FIG. 5B show schematically a perspective view of the actuator mechanism 300 including connection means 105*a* for connecting the housing 100 comprising the cryogenic fluid cartridge 110, whereby said cryogenic fluid is preferably carbon dioxide. FIGS. 5A and 5B show a series of hook elements 106*a*', 106*a*", etc. which ensure unidirectional engaging of the housing 100 and the actuator mechanism 300. FIG. 5C shows a schematic cross-sectional view of the same actuator mechanism as FIG. 5A. FIG. 5D shows a schematic side view of the same actuator mechanism as FIG. 5A.

Figure 6A:
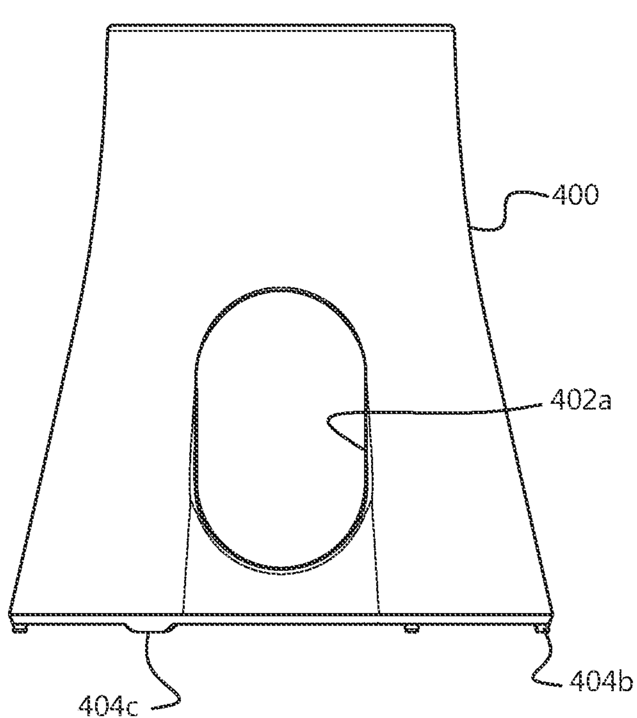
FIG. 6A shows a schematic side view of the closing cap 400.
Figure 6B:
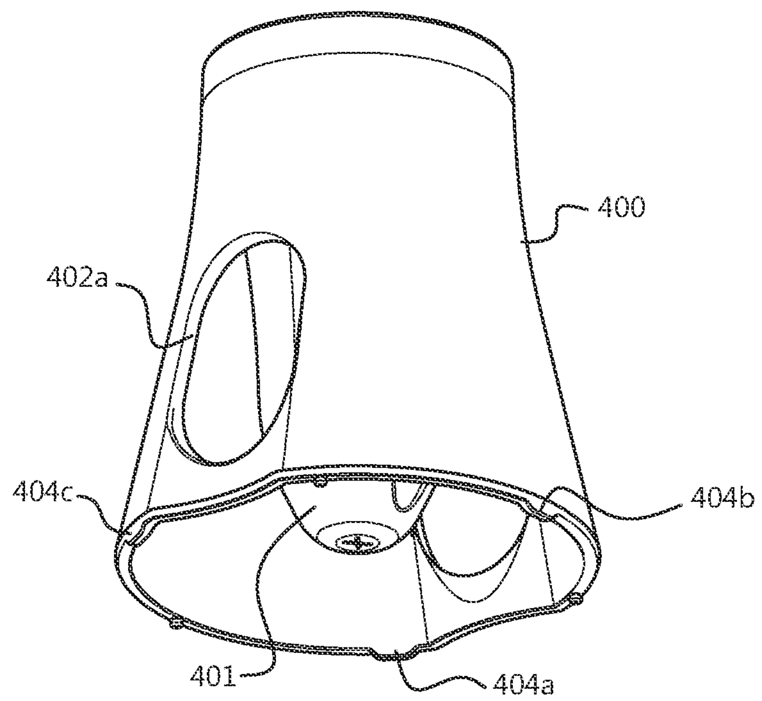
FIG. 6B shows a schematic perspective view of the closing cap 400.
Figure 6C:
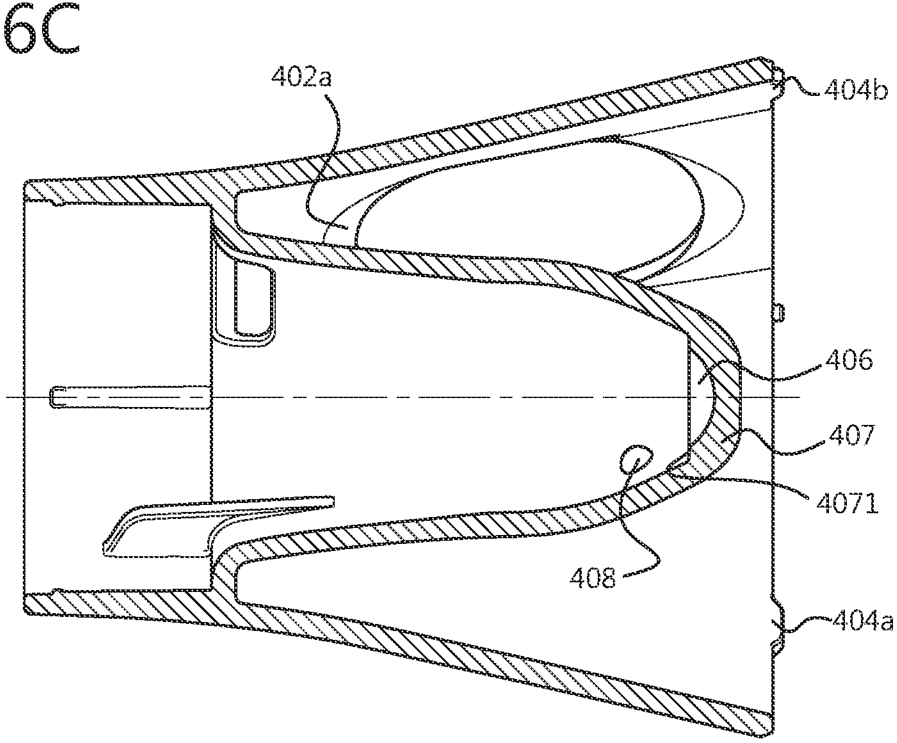
FIG. 6C shows schematically a cross-sectional view of the closing cap 400.
Figure 6D:
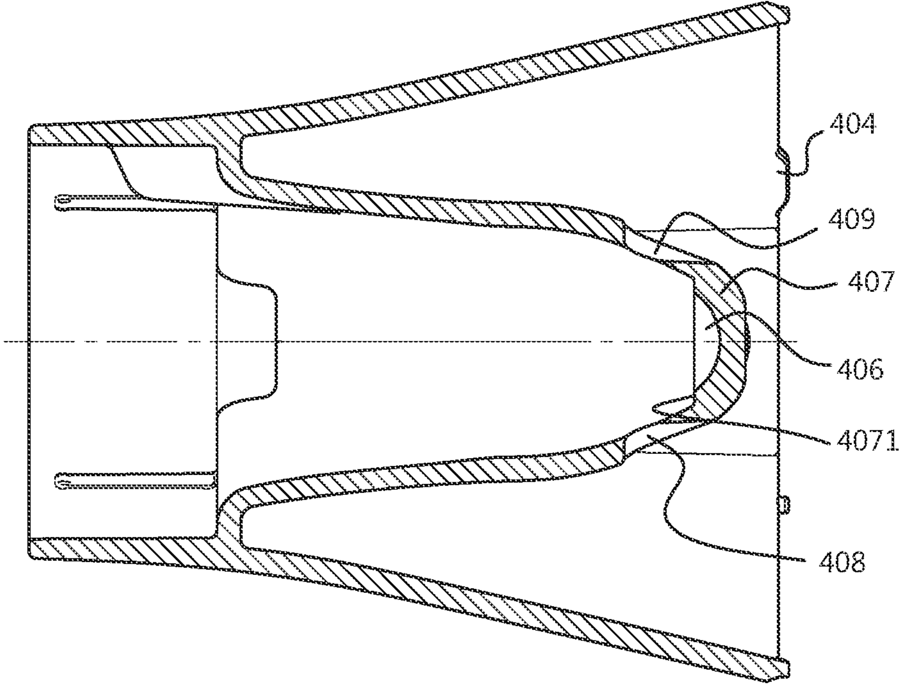
FIG. 6D shows schematically a cross-sectional view of the closing cap 400, whereby the cross-section is taken in the longitudinal direction of the device, perpendicular to the cross-section of FIG. 6C.

FIG. 6A shows a schematic side view of the closing cap 400. FIG. 6B shows a schematic perspective view of the closing cap 400. FIG. 6C shows schematically a cross-sectional view of the closing cap 400. FIG. 6C shows additionally a supporting rim 4071 within the cup 407 which is intended to give a counteracting pressure on the applicator surface 201 when the closing cap is in the engaged position and when the device is actuated. The pressure on the applicator surface 201 engages the actuation mechanism 300, which accordingly opens the ball valve mechanism and allows the outflow of the cryogenic fluid, preferably carbon dioxide. FIG. 6D shows schematically a cross-sectional view of the closing cap 400, as in FIG. 6C, whereby the cross-section is taken in the longitudinal direction of the device, perpendicular to the cross-section of FIG. 6C. FIG. 6D shows in further detail the provision of ventilation holes 408 and 409 to allow for evacuation of excess cryogenic fluid gases, whereby said cryogenic fluid is preferably carbon dioxide.

Figure 7A:
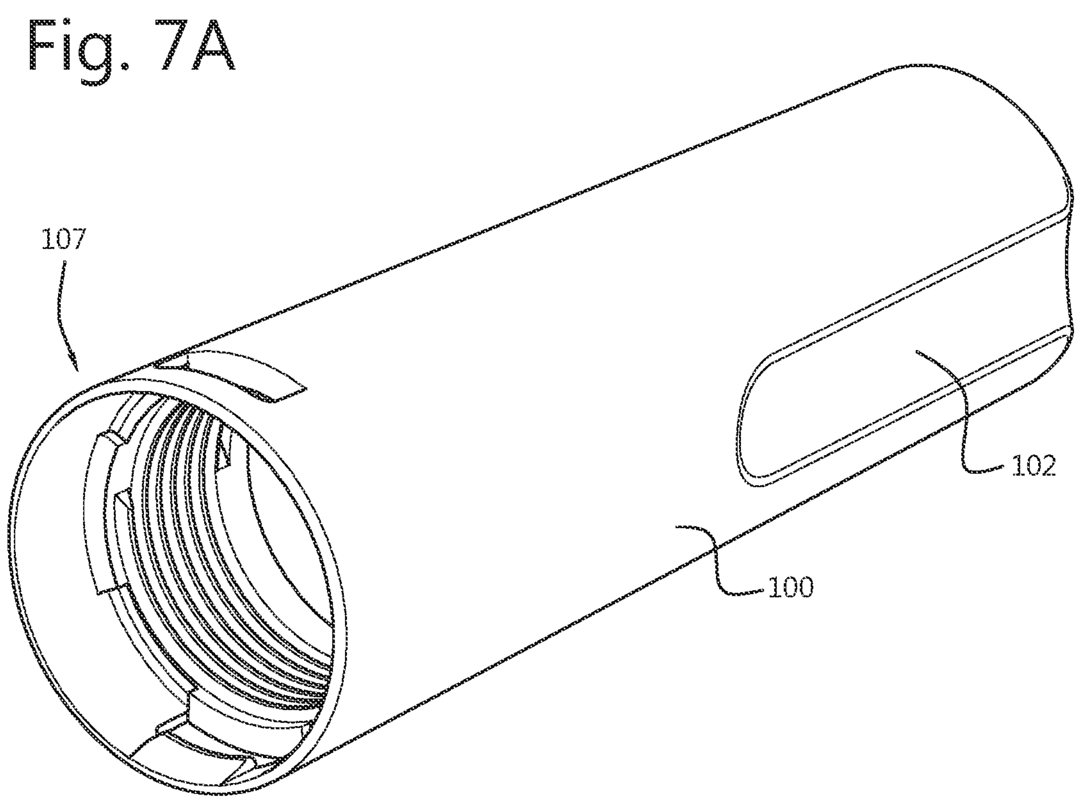
FIG. 7A shows schematically a perspective view on the housing 100 with grip recession 102.
Figure 7B:
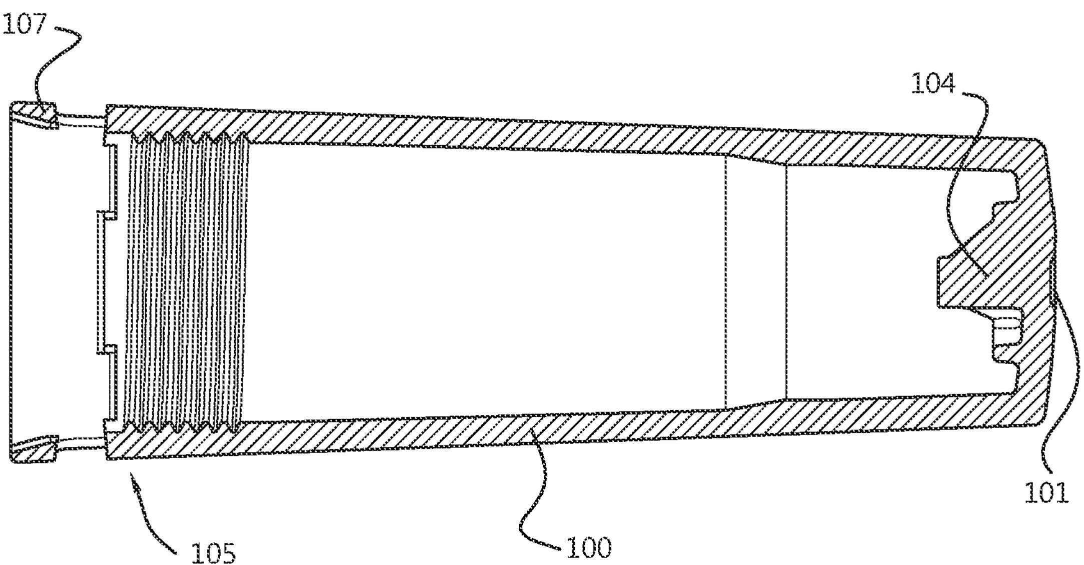
FIG. 7B shows schematically a cross-sectional view of the casing 100.

FIG. 7A shows schematically a perspective view on the housing 100 with grip recession 102. FIG. 7B shows schematically a cross-sectional view of the casing 100.

Example 2

Figure 8A:
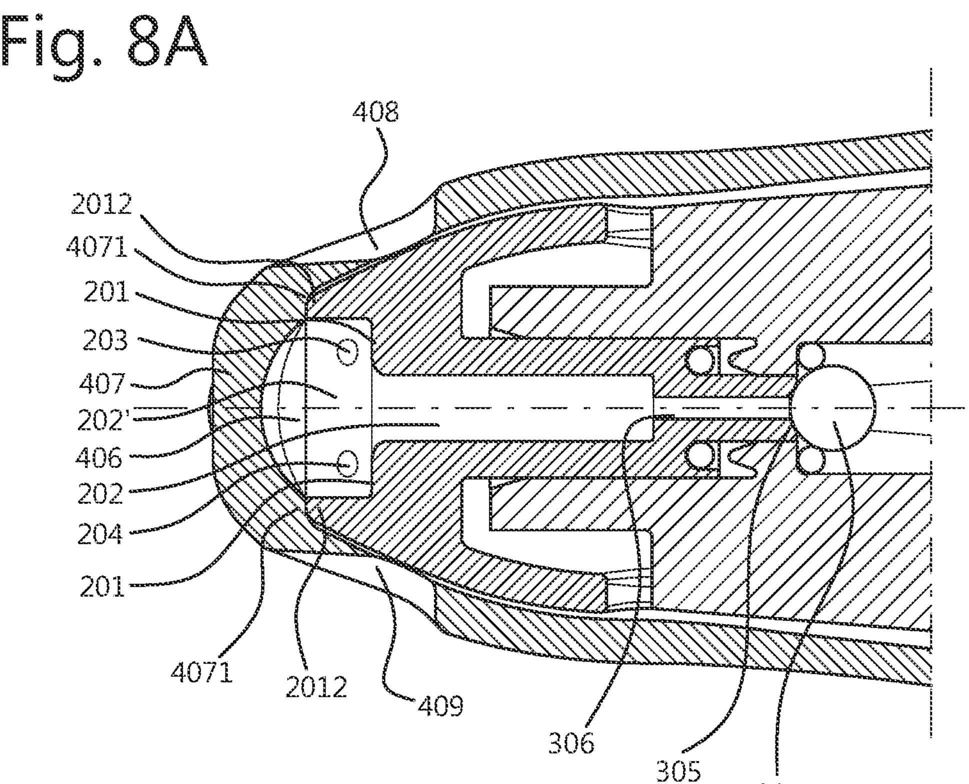
FIG. 8A shows schematically a cross-sectional view in the longitudinal direction of a device according to the invention comprising a closing cap 400.
Figure 8B:
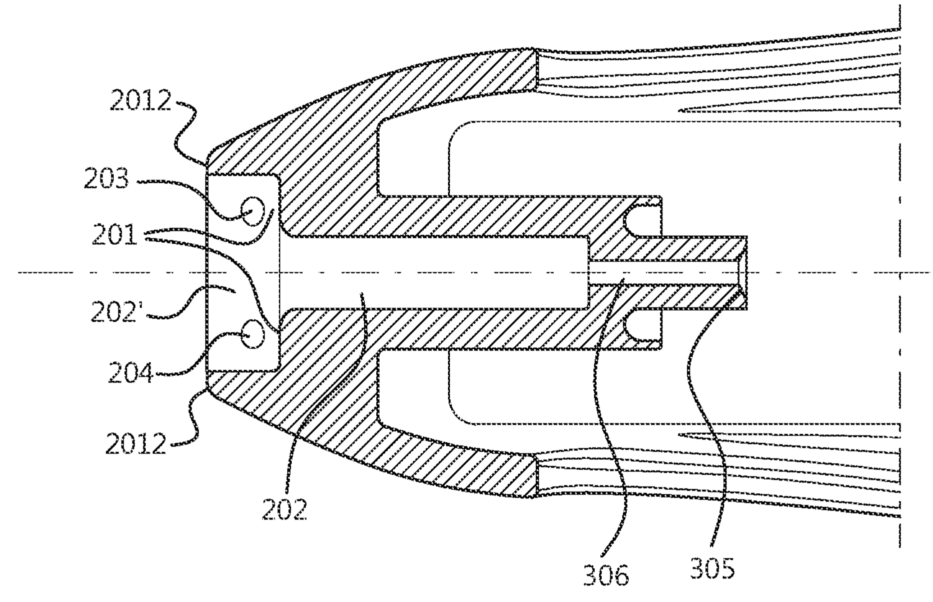
FIG. 8B shows schematically a cross-sectional view in the longitudinal direction of a device according to the invention without a closing cap 400.

An alternative embodiment of the invention is shown in FIG. 8. FIG. 8A shows schematically a cross-sectional view in the longitudinal direction of a device according to the invention comprising a closing cap 400. FIG. 8B shows schematically a cross-sectional view in the longitudinal direction of a device according to the invention without a closing cap 400.

The embodied device according to Example 2 and FIG. 8 corresponds to the embodiment according to Example 1 and FIG. 1-7, the sole difference being that the applicator surface 201 is flat and venting holes 203 and 204 are provided downstream of the applicator surface 201. The cryogenic fluid tablet, preferably the dry ice carbon dioxide tablet is now formed within the space within the sublimation chamber 406 and the part of the internal channel 202' downstream of the applicator surface. The device can be used without the closing cap 400. To this aim, the device is actuated by pressing the tip onto a surface, thereby actuating the cryogenic fluid flow, preferably the carbon dioxide flow from the cartridge through the internal channel 202-202'. Dry ice forms within the internal channel 202' and partly enters the venting holes 203, 204. Accordingly, the cryogenic fluid tablet, preferably carbon dioxide tablet is formed onto the applicator surface 201 and is withheld onto the applicator surface 201 by anchoring of the dry ice tablet within the venting holes 203, 204. Likewise, the device can be used with the closing cap 400, whereby the cryogenic fluid tablet, preferably carbon dioxide tablet forms within the volume formed by the sublimation chamber 406 and the internal channel 202'.

In a further embodiment, the applicator surface 201 may have a higher surface roughness.

Example 3

Figure 9D:
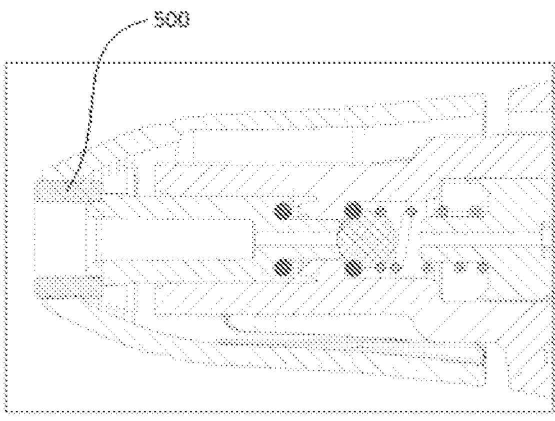

A preferred embodiment of the invention is shown in FIGS. 9A, 9C and 9D. In said preferred embodiment, applicator surface 201 comprises the adhesion surface ring 500, preferably made of thermoplastic polymer such as UHMW-PE. Said adhesion surface ring controls the turbulence during $CO_2$ expansion and improves adhering of the formed $CO_2$ tablet to the applicator tip.

In Table 1 are summarised the results of the comparative surface adhesion test, which show the adhesion of the carbonic ice tablet. Two groups of the devices, namely devices without the adhesion surface ring and with adhesion surface ring were tested in parallel for a) visual inspection of the carbonic ice tablet formed and b) table-top drop tests (+/−10 cm) on the edge of the table to evaluate surface adhesion of the carbonic ice tablet to the device.

In total 20 carbonic ice tablets were formed and analyzed:

A. 10 tablets formed in a device comprising applicator surface without the adhesion surface ring;

B. 10 tablets formed a device comprising applicator surface with the adhesion surface ring of the invention.

The carbonic ice tablets were visually inspected if they feature a semi-spherical shape and smooth surface ("Visual inspection") and if it releases upon dropping the device on the table top ("Table drop test"). The results of the tests are given below in Table 1.

TABLE 1

Results of the visual inspection and the table drop test of carbonic ice tablets obtainable by a cryogenic device featuring A) applicator surface without the adhesion surface ring; and B) applicator surface with the adhesion surface ring.

| Tablet N° | Visual inspection | Table top drop test |
|---|---|---|
| 1-A | Pass | Fail |
| 2-A | Pass | Pass |
| 3-A | Pass | Fail |
| 4-A | Pass | Fail |
| 5-A | Pass | Pass |
| 6-A | Pass | Fail |
| 7-A | Pass | Pass |
| 8-A | Pass | Pass |
| 9-A | Pass | Fail |
| 10-A | Pass | Fail |
| 11-B | Pass | Pass |
| 12-B | Pass | Pass |
| 13-B | Pass | Pass |
| 14-B | Pass | Pass |
| 15-B | Pass | Pass |
| 16-B | Pass | Pass |
| 17-B | Pass | Pass |
| 18-B | Pass | Pass |
| 19-B | Pass | Pass |
| 20-B | Pass | Pass |

CONCLUSION

While 100% of all device with current stem-design pass the visual inspection, 60% fails the tablet-top drop test.

The new design (incl. adhesion surface ring), successfully passes both visual inspection (100%) and the table-drop test (100%).

This experimental data substantiates the improved adhesion of the carbonic ice tablet after introduction of the new design (incl. adhesion surface ring).

It is supposed that the present invention is not restricted to any form of realization described previously and that some modifications can be added to the presented example of fabrication without reappraisal of the appended claims. For example, the present invention has been described referring to the integrated actuator assembly comprising two spring leaves, but it is clear that the invention can be applied to the integrated actuator assembly comprising three or more spring leaves.

The invention claimed is:

1. Device for the topical cryotherapy of dermatological disorders, including warts, in a subject in need thereof, the device comprising:

a housing for holding a pressurized carbon dioxide cartridge, said housing defining a cavity sized to receive and support said cartridge; an applicator nozzle comprising (i) an internal channel disposed in the housing for guiding the outflow of carbon dioxide from said pressurized carbon dioxide cartridge, and (ii) an applicator surface formed at an end of the housing onto which carbon dioxide ice may be formed, wherein the applicator surface defines an outlet of the internal channel;

an actuator mechanism for controlling an outflow of carbon dioxide from said pressurized carbon dioxide cartridge to said applicator nozzle, which actuator mechanism is movable between a first, closed position and between a second, open position; and further comprising a closing cap, detachably provided across from said applicator surface, said closing cap comprising a cup which, in an arranged position, faces towards said applicator surface, thereby forming a sublimation chamber between said cup of said closing cap and said applicator surface; whereby said cup, in said arranged position, is configured to prevent the outflow of carbon dioxide gas from said sublimation chamber so that solid carbon dioxide ice forms in the sublimation chamber and is attached to and covers the applicator surface;

said applicator nozzle defining a venting hole upstream of said applicator surface, said venting hole in fluid communication with said internal channel, said cup further defining a venting cavity, and whereby said venting hole and said venting cavity, in said arranged position, are aligned to permit evacuation of carbon dioxide from said internal channel and pressure to drop in said sublimation chamber.

2. The device according to claim 1, wherein said actuator mechanism comprises a ball valve, whereby said ball valve comprises a ball resiliently biased against a ball seat, and wherein said ball seat comprises a concave contact surface oriented towards said ball, and wherein said concave contact surface comprises one or more flow restriction channels for conducting carbon dioxide and for restricting its flow.

3. The device according to claim 2, wherein said concave contact surface comprises two or more flow restriction channels.

4. The device according to claim 1, wherein said applicator surface comprises an adhesion surface ring made of ultra-high-molecular-weight polyethylene.

5. The device according to claim 1, wherein said applicator surface has a surface roughness of greater than 250 μm and said cup has a surface roughness of not greater than 250 μm, as determined by ISO 25178.

6. The device according to claim 1, wherein the applicator surface of said applicator nozzle has a greater surface roughness than the contact surface of said cup.

7. Kit for assembling a device for the topical cryotherapy of dermatological disorders, such as warts, in a subject in need thereof, the kit comprising:

a housing for holding a pressurized carbon dioxide cartridge, said housing defining a cavity sized to receive and support said cartridge;

a pressurized carbon dioxide cartridge;

an applicator nozzle comprising (i) an internal channel disposed in the housing for guiding the outflow of carbon dioxide from said pressurized carbon dioxide cartridge, and (ii) an applicator surface formed at an end of the housing preferably comprising an adhesion surface ring onto which a carbon dioxide ice tablet may be formed, wherein the applicator surface defines an outlet of the internal channel;

an actuator mechanism for controlling an outflow of carbon dioxide from said pressurized carbon dioxide cartridge to said applicator nozzle, which actuator mechanism is movable between a first, closed position and between a second, open position; and further comprising a closing cap, detachably provided across from said applicator surface, said closing cap comprising a cup which, in an arranged position, faces towards said applicator surface, thereby forming a sublimation chamber between said cup of said closing cap and said applicator surface; whereby said cup, in said arranged position, is configured to prevent the outflow of carbon dioxide gas from said sublimation chamber so that solid carbon dioxide ice forms in the sublimation chamber and is attached to and covers the applicator surface;

said applicator nozzle defining a venting hole upstream of said applicator surface, said venting hole in fluid communication with said internal channel, said cup further defining a venting cavity, and whereby said venting hole and said venting cavity, in said arranged position, are aligned to permit evacuation of carbon dioxide from said internal channel and pressure to drop in said sublimation chamber.

8. The device of claim 1, wherein the device is configured to be operable in:

a first configuration in which said closing cap is attached across from said applicator surface so as to form the sublimation chamber, permitting solid carbon dioxide ice to form on and attach to the applicator surface upon actuation of said actuator mechanism, and a second configuration in which said closing cap is detached from the device, with the solid carbon dioxide ice remaining attached to said applicator surface and covering said applicator surface for application of said solid carbon dioxide ice to a dermatological disorder.

9. The device of claim 1, wherein:

the device and closing cap are movable between a first configuration and a second configuration, in the first configuration, when the closing cap is attached to the device, a hole within the closing cap is aligned with a ventilation cavity within the applicator nozzle, thereby allowing carbon dioxide gas to evacuate the device and the closing cap; and in the second configuration, when the closing cap is removed from the device, the ventilation cavity and the hole are no longer aligned.

* * * * *